US012213858B2

(12) United States Patent
Raslambekov

(10) Patent No.: US 12,213,858 B2
(45) Date of Patent: Feb. 4, 2025

(54) SYSTEMS AND METHODS FOR DETERMINING AN ORTHODONTIC TREATMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 414 days.

(21) Appl. No.: 17/847,135

(22) Filed: Jun. 22, 2022

(65) Prior Publication Data

US 2023/0172691 A1 Jun. 8, 2023

Related U.S. Application Data

(63) Continuation-in-part of application No. 17/544,146, filed on Dec. 7, 2021, now Pat. No. 11,399,917.

(51) Int. Cl.
*A61C 7/08* (2006.01)
*A61C 7/00* (2006.01)
*G06T 19/20* (2011.01)

(52) U.S. Cl.
CPC .............. *A61C 7/08* (2013.01); *A61C 7/002* (2013.01); *G06T 19/20* (2013.01); *A61C 2007/004* (2013.01); *G06T 2207/30036* (2013.01)

(58) Field of Classification Search
CPC ..... A61C 7/002; A61C 7/08; A61C 2007/004; G06T 7/12; G06T 19/20; G06T 2207/30036; G16H 20/30; G16H 20/40; G16H 30/40; G16H 50/50
See application file for complete search history.

(56) References Cited

U.S. PATENT DOCUMENTS

| | | | |
|---|---|---|---|
| 7,354,268 B2 | 4/2008 | Raby et al. | |
| 8,199,988 B2 | 6/2012 | Marshall et al. | |
| 9,626,462 B2 | 4/2017 | Somasundaram et al. | |
| 10,758,322 B2 | 9/2020 | Pokotilov et al. | |
| 10,856,954 B1 | 12/2020 | Raslambekov | |
| 10,950,061 B1 | 3/2021 | Raslambekov | |
| 10,993,782 B1 | 5/2021 | Raslambekov | |
| 11,026,767 B1 | 6/2021 | Raslambekov | |
| 11,055,850 B1 | 7/2021 | Raslambekov | |
| 11,191,618 B1 | 12/2021 | Raslambekov | |

(Continued)

OTHER PUBLICATIONS

Sinthanayothin et al.,"Orthodontics Treatment Simulation by Teeth Segmentation and Setup", Published on Jun. 2008, DOI: 10.1109/ECTICON.2008.4600377.

(Continued)

*Primary Examiner* — Ping Y Hsieh
*Assistant Examiner* — Jose M Torres
(74) *Attorney, Agent, or Firm* — BCF LLP

(57) ABSTRACT

A method and a system for planning an orthodontic treatment are provided. The method comprises: acquiring an arch form 3D digital model including a representation of the given tooth in a current position thereof within a subject's gingiva; determining an initial crown reference point and an initial root reference point; obtaining a target position of the given tooth within the arch form 3D digital model; determining a number of steps for the given tooth to displace from the current position to the target position thereof in the course of the orthodontic treatment; and storing data indicative of the number of steps associated with the given tooth for use in the planning the orthodontic treatment.

20 Claims, 10 Drawing Sheets

(56) References Cited

U.S. PATENT DOCUMENTS

| | | |
|---|---|---|
| 11,191,620 B1 | 12/2021 | Raslambekov |
| 11,259,897 B1 | 3/2022 | Raslambekov |
| 2020/0214801 A1 | 7/2020 | Wang et al. |

OTHER PUBLICATIONS

Colosi et al. "Modeling and Simulation of Controlled Orthodontic Tipping and Translation of Single-rooted Teeth", 2008 IEEE International Conference on Automation, Quality and Testing, Robotics, Published on Jun. 2008, pp. 1-5, DOI:10.1109/AQTR.2008.4588901.

Seo et al., "Comparative Analysis of Stress in the Periodontal Ligament and Center of Rotation in the Tooth after Orthodontic Treatment Depending on Clear Aligner Thickness—Finite Element Analysis Study", Published on Jan. 9, 2021, pp. 1-17, https://doi.org/10.3390/ma14020324.

Penedo et al., "3D simulation of orthodontic tooth movement", Dental Press Journal of Orthodontics, online, Nov. 11, 2010, pp. 98-108, https://doi.org/10.1590/S2176-94512010000500012.

Pratiwi et al., "Simulation of Stress Distribution on the Upper First Molar and Alveolar Bone with the Transpalatal Arch and Upper Second Molar Using Finite Element Analysis", Pesquisa Brasileira em Odontopediatra e Clinica Integrada, Published on Jul. 1, 2019, DOI: http://doi.org/10.4034/PBOCI.2019.191.110.

U.S. Appl. No. 16/704,718, filed Dec. 5, 2019.

A # SYSTEMS AND METHODS FOR DETERMINING AN ORTHODONTIC TREATMENT

CROSS-REFERENCE

The present application is a Continuation-In-Part application of U.S. patent application Ser. No. 17/544,146 filed on Dec. 7, 2021, and entitled "SYSTEMS AND METHODS FOR DETERMINING AN ORTHODONTIC TREATMENT", the content of which is incorporated herein by reference in its entirety.

FIELD

The present technology relates generally to systems and methods for determining an orthodontic treatment for a subject, and, in particular, to methods and systems for determining a tooth trajectory for a given tooth of the subject.

BACKGROUND

In orthodontics, planning an orthodontic treatment for a subject may include determining a tooth trajectory for each tooth of a subject's arch form. This may further include modelling tooth movements of a given tooth in the course of the planned orthodontic treatment using the respective 3D digital model of the given tooth: from an initial (current) position to a target position of the given tooth, the target position being typically associated with alignment of the given tooth within the subject's arch form.

For example, the tooth trajectory of the given tooth may be determined as a trajectory of a given point thereof, such as a center of resistance (CR) point of the given tooth typically determined to be located on a tooth axis thereof. Further, the so determined tooth trajectory may be divided into a number of segments each of which is predetermined to be no longer than a certain safety threshold such that a displacement of the given tooth along a given segment of the tooth trajectory would not cause damage to surrounding tissues of the given tooth, such as a periodontal ligament (PDL) thereof.

Further, once the tooth movements have been modelled, an orthodontic device, such as an aligner (or a set thereof), may be produced and applied to the subject's arch form to exert a respective external force onto the given tooth causing it to move, along a given segment of the so determined tooth trajectory, towards the target position.

However, the orthodontic treatment planned based on the so determined tooth trajectory may still cause certain damages to the PDL of the given tooth. For example, the given tooth may be mesially inclined within a subject's gingiva. As a result, in the course of the orthodontic treatment, while the CR point of the given tooth moves towards the target position thereof along the given segment of the tooth trajectory, other points of the given tooth lying on the tooth axis within at least one of the crown portion and the root portion thereof may displace at a longer distance than that of the given segment. This may cause excessive strain to the PDL of the given tooth resulting in damage thereof either at the crown portion or the root portion thereof, respectively.

SUMMARY

Certain prior art approaches for modelling tooth movements have been proposed.

U.S. Pat. No. 9,626,462-B2 issued on Apr. 18, 2017, assigned to 3M Innovative Properties Co., and entitled "DETECTING TOOTH WEAR USING INTRA-ORAL 3D SCANS" discloses a method for detecting tooth wear using digital 3D models of teeth taken at different times. The digital 3D models of teeth are segmented to identify individual teeth within the digital 3D model. The segmentation includes performing a first segmentation method that over segments at least some of the teeth within the model and a second segmentation method that classifies points within the model as being either on an interior of a tooth or on a boundary between teeth. The results of the first and second segmentation methods are combined to generate segmented digital 3D models. The segmented digital 3D models of teeth are compared to detect tooth wear by determining differences between the segmented models, where the differences relate to the same tooth to detect wear on the tooth over time.

U.S. Pat. No. 10,758,322-B2 issued on Sep. 1, 2020, assigned to Align Technology Inc., and entitled "VIRTUALLY REPRESENTING AN ORTHODONTIC TREATMENT OUTCOME USING AUTOMATED DETECTION OF FACIAL AND DENTAL REFERENCE OBJECTS" discloses a computer-implemented method for virtually representing an orthodontic treatment outcome using automated detection of facial and dental reference objects. The computer-implemented method may involve modeling initial positions of an orthodontic patient's teeth in a three-dimensional (3D) virtual model and determining the effect of application of various force systems applied through an orthodontic treatment plan on the patient's teeth. Images of the patient's face may be used to identify facial reference objects. Dental reference objects of the patient's dentition may be identified from the 3D virtual model. A relationship between the facial reference objects and the dental reference objects may form the basis of modifications to the orthodontic treatment plan and/or modeling final orthodontic positions of the orthodontic treatment plan.

Developers of the present technology have appreciated that modelling movements of the given tooth at reference points on a tooth axis of the given tooth corresponding to vertical boundaries of the PDL at the crown portion and the root portion, respectively, may address the above-identified technical problem. More specifically, the developers have realized that overstretching of the PDL causing the damage thereof can be averted if a number of steps of the orthodontic treatment is determined based on a trajectory of that reference point of the given tooth which is a most distant one from its respective target position. In other words, at least some non-limiting embodiments of the present technology are directed to determining the tooth trajectory of the given tooth as the trajectory of that point thereof lying on the tooth axis along the PDL, which is, in the course of the orthodontic treatment, to displace at a longer distance than others while the given tooth moves to the target position thereof.

Further, the so determined trajectory can be segmented such that each of the segments does not exceed the predetermined safety distance threshold. Further, a respective orthodontic appliance can be produced and further applied to the given tooth to cause the so determined reference point thereof to move along a given segment of the so determined trajectory.

As a result, during the orthodontic treatment, when the so determined reference point of the given tooth from its respective current position is caused to displace at a length of the given segment, other points lying on the tooth axis along the PDL would displace at respective shorter distances than the length of the given segment.

By doing so, non-limiting embodiments of the present technology may prevent excessive strain to the PDL at any point thereof within its vertical boundaries during the movement of the given tooth to its target position, which may further allow for more predictive planning of orthodontic treatments and elevated safety and effectiveness of implementation thereof.

Thus, in accordance with a first broad aspect of the present technology, there is provided a computer-implemented method of planning an orthodontic treatment for a given tooth of a subject. The method is executable by a processor. The method comprises: acquiring, by the processor, an arch form 3D digital model including a representation of a crown portion of the given tooth in a current position thereof within a subject's gingiva, the given tooth being associated with a predetermined longitudinal reference axis; determining, by the processor, on the predetermined longitudinal reference axis, an initial crown reference point and an initial root reference point, the initial crown reference point being indicative of a first vertical boundary of a periodontal ligament around the given tooth at the crown portion thereof; and the initial root reference point being indicative of a second vertical boundary of the periodontal ligament around the given tooth at a root portion thereof; obtaining, by the processor, a target position of the given tooth within the arch form 3D digital model; determining, by the processor, based on the target position of the given tooth, a target crown reference point and a target root reference point, thereby defining: a crown reference line extending between the initial crown reference point and the target crown reference point. The crown reference line may be representative of a crown trajectory, along which the crown portion of the given tooth is to be moved while the given tooth is moving from the current position to the target position thereof. The method further comprises defining a root reference line extending between the initial root reference point and the target root reference point. The root reference line is representative of a root trajectory, along which the root portion of the given tooth is to be moved while the given tooth is moving from the current position to the target position thereof. The method may further comprise determining, by the processor, a number of steps for the given tooth to displace from the current position to the target position thereof in the course of the orthodontic treatment by determining a respective number of segments, into which each one of the crown reference line and the root reference line is to be segmented. The determining may include: iteratively minimizing the respective number of segments associated with a longer one of the crown reference line and the root reference line until a longest segment thereof is no longer than a predetermined segment length threshold; determining, by the processor, the number of steps for the given tooth to displace to the target position as being the respective number of segments associated with the longer one of the crown reference line and the root reference line; and storing, by the processor, data indicative of the number of steps associated with the given tooth for use in the planning the orthodontic treatment.

In some implementations of the method, the predetermined longitudinal reference axis is a central tooth axis of the given tooth having been predetermined based on the representation of the crown portion of the given tooth within the arch form 3D digital model.

In some implementations of the method, determining, on the predetermined longitudinal reference axis, the initial crown reference point includes: obtaining, by the processor, a segmentation loop, the segmentation loop segmenting, in the arch form 3D digital model, the crown portion of the given tooth from the subject's gingiva; determining, by the processor, a center of the segmentation loop on the predetermined longitudinal reference axis of the given tooth; and offsetting the center of the segmentation loop along the predetermined longitudinal axis towards the root portion at a predetermined crown offset distance.

In some implementations of the method, the determining the center of the segmentation loop comprises: projecting, over a respective normal vector, each vertex representative of the segmentation loop of the given tooth on the predetermined longitudinal reference axis; and determining the center of the segmentation loop as a midpoint amongst projected vertices on the predetermined longitudinal reference axis.

In some implementations of the method, the determining the center of the segmentation loop comprises: generating, within the arch form 3D digital model, a bounding box around the segmentation loop; and determining the center of the segmentation loop as a center of a segment of the predetermined longitudinal reference axis formed by an intersection thereof with the bounding box.

In some implementations of the method, the determining, on the predetermined longitudinal reference axis, the initial root reference point includes determining, in the arch form 3D digital model, a point corresponding to a root apex of a longest root of the root portion of the given tooth.

In some implementations of the method, the determining the point corresponding to the root apex is based on reference data associated with the given tooth, the reference data comprising data of an approximate length associated with the root portion of the given tooth.

In some implementations of the method, the determining the initial root reference point further comprises offsetting the point corresponding to the root apex of the given tooth along the predetermined longitudinal reference axis towards the crown portion at a predetermined root offset distance.

In some implementations of the method, the initial root reference point is a center of resistance associated with the given tooth.

In some implementations of the method, the predetermined segment length threshold has been determined such that a movement of the given tooth along a given segment of any one of the crown reference line and the root reference line does not cause damage to the periodontal ligament of the given tooth.

In some implementations of the method, the orthodontic treatment includes applying a respective orthodontic appliance at each step of the number of steps.

In some implementations of the method, each one of the number of steps is of a same length.

In some implementations of the method, the applying the respective orthodontic appliance is for a predetermined treatment interval.

In accordance with a second broad aspect of the present technology, there is provided a system for planning an orthodontic treatment for a given tooth of a subject. The system may include a processor and a non-transitory computer-readable medium storing instructions. Further, the processor, upon executing the instructions, is configured to: acquire an arch form 3D digital model including a representation of a crown portion of the given tooth in a current position thereof within a subject's gingiva, the crown portion of the given tooth from the subject's gingiva, the given tooth being associated with a predetermined longitudinal reference axis; determine, on the predetermined longitudinal reference axis, an initial crown reference point and an initial root reference point, the initial crown reference point being indicative of a first vertical boundary of a periodontal ligament around the given tooth at the crown portion thereof; and the initial root reference point being indicative of a second vertical boundary of the periodontal ligament around the given tooth at a root portion thereof; obtain a target position of the given tooth within the arch form 3D digital model; determine, based on the target position of the given tooth, a target crown reference point and a target root reference point, thereby defining a crown reference line extending between the initial crown reference point and the target crown reference point. The crown reference line can be representative of a crown trajectory, along which the crown portion of the given tooth is to be moved while the given tooth is moving from the current position to the target position thereof. The processor can further be configured to define a root reference line extending between the initial root reference point and the target root reference point. The root reference line can thus be representative of a root trajectory, along which the root portion of the given tooth is to be moved while the given tooth is moving from the current position to the target position thereof. Further, the processor can be configured to determine a number of steps for the given tooth to displace from the current position to the target position thereof in the course of the orthodontic treatment by determining a respective number of segments, into which each one of the crown reference line and the root reference line is to be segmented. To determine the respective number of segments, the processor can be configured to iteratively minimize the respective number of segments associated with a longer one of the crown reference line and the root reference line until a longest segment thereof is no longer than a predetermined segment length threshold. The processor can further be configured to determine the number of steps for the given tooth to displace to the target position as being the respective number of segments associated with the longer one of the crown reference line and the root reference line; and store, in the non-transitory computer-readable medium, data indicative of the number of steps associated with the given tooth for use in the planning the orthodontic treatment.

In some implementations of the system, to determine, on the predetermined longitudinal reference axis, the initial crown reference point, the processor is further configured to: obtain a segmentation loop, the segmentation loop segmenting, in the arch form 3D digital model; determine a center of the segmentation loop on the predetermined longitudinal reference axis of the given tooth; and offset the center of the segmentation loop along the predetermined longitudinal axis towards the root portion at a predetermined crown offset distance.

In some implementations of the system, to determine the center of the segmentation loop, the processor is configured to: project, over a respective normal vector, each vertex representative of the segmentation loop of the given tooth on the predetermined longitudinal reference axis; and determine the center of the segmentation loop as a midpoint amongst projected vertices on the predetermined longitudinal reference axis.

In some implementations of the system, to determine the center of the segmentation loop, the processor is configured to: generate, within the arch form 3D digital model, a bounding box around the segmentation loop; and determine the center of the segmentation loop as a center of a segment of the predetermined longitudinal reference axis formed by an intersection thereof with the bounding box.

In some implementations of the system, to determine, on the predetermined longitudinal reference axis, the initial root reference point, the processor is configured to determine, in the arch form 3D digital model, a point corresponding to a root apex of a longest root of the root portion of the given tooth.

In some implementations of the system, the processor is configured to determine the point corresponding to the root apex based on reference data associated with the given tooth, the reference data comprising data of an approximate length associated with the root portion of the given tooth.

In some implementations of the system, to determine the initial root reference point further, the processor is further configured to offset the point corresponding to the root apex of the given tooth along the predetermined longitudinal reference axis towards the crown portion at a predetermined root offset distance.

In the context of the present specification, the term "orthodontic treatment" is broadly referred to as any type of medical intervention aimed at correcting malocclusions associated with the subject's teeth or moving the patient's teeth for any reason, including surgical and non-surgical manipulations, such as, but not limited to, using one or more of aligners, brackets, multi-strand wires, strips, retainers, and plates. Further, the orthodontic treatment, as referred to herein, may be determined manually by a professional practitioner (such as an orthodontist, a maxillofacial surgeon, for example), automatically by a specific software based on image data and input parameters associated with the subject, and/or a combination of manual and automatic.

Also, as used herein, determining the orthodontic treatment may include verification of an already determined orthodontic treatment, for example, by modelling an effect of the determined orthodontic treatment using respective 3D models (such as 3D meshes) of the subject's teeth. The verification may be conducted, for example, to ensure safety and effectiveness of the determined orthodontic treatment for the subject.

In the context of the present specification, the term "CR point" of a given body is broadly referred to as a point, at which imposing a given mechanical force results in a translational movement (or otherwise, a bodily movement) of the given body in a direction of the given mechanical force, along a line of action thereof. As used herein, the CR point is mostly determined for restrained bodies, such as teeth, and, in a sense, may be considered as an equivalent to a center of gravity point (center of mass point) for unrestrained (free) bodies.

Further, in the context of the present specification, the term "tooth axis" of a given tooth denotes a line extending through the given tooth lengthwise, through a crown portion and a root portion thereof, around which mass of the given tooth as well as anatomical features (such as lobes, developmental grooves, and marginal ridges thereof, for example) thereof are distributed substantially symmetrically.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

Figure 1:
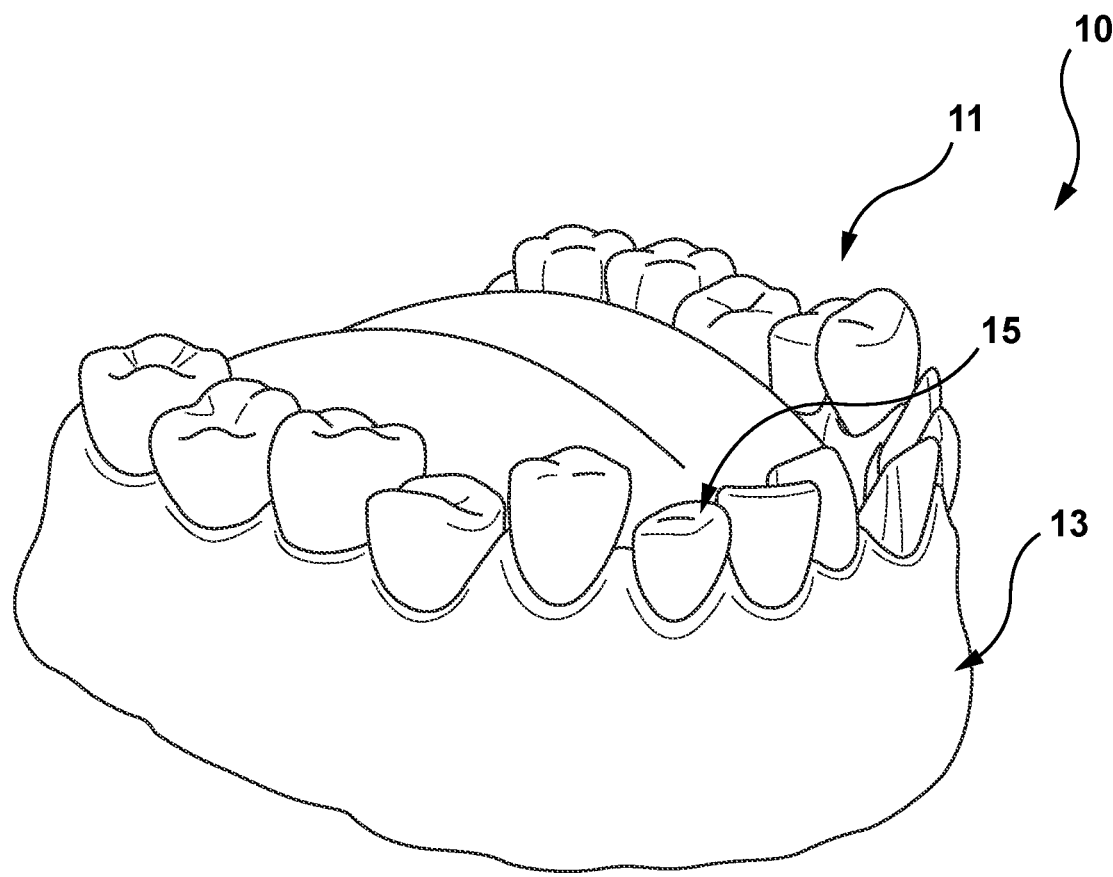
FIG. 1 depicts a perspective view of a lower arch form of a subject depicting examples of malocclusions of some of subject's teeth, in accordance with certain non-limiting embodiments of the present technology.

It should be noted that, unless otherwise explicitly specified herein, the drawings are not to scale.

DETAILED DESCRIPTION

Certain aspects and embodiments of the present technology are directed to methods of and systems for determining a tooth trajectory for a given tooth of a subject. Further, based on the tooth trajectory, an orthodontic treatment for the subject may be planned.

More specifically, certain aspects and embodiments of the present technology comprise a computer-implemented method of determining, based on a tooth 3D digital model of the given tooth, a reference point thereof used for tracing the tooth trajectory of the given tooth when modelling movements thereof from its current position to its target position in the course of the orthodontic treatment. For example, the so determined tooth trajectory can be segmented into a plurality of segments, for each of which a respective orthodontic appliance can be produced and further applied to the given tooth to cause it to move along a given segment towards the target position thereof.

Certain embodiments of the present technology minimize, reduce or avoid some of the problems noted with the prior art. For example, implementing certain embodiments of the present technology, may allow increasing safety and efficiency of orthodontic treatments.

For example, increasing safety can be achieved by determining the reference point for generating the tooth trajectory of the given tooth as a point located on a tooth axis of the given tooth on a level of one of vertical boundaries of a periodontium ligament (PDL) around the given tooth. More specifically, the reference point can be determined such that, during the implementation of the orthodontic treatment, it would be that point lying on the tooth axis along the PDL which is to displace, during the orthodontic treatment, at a longer distance than any other point defined on the tooth axis along of the PDL. Further, a length of the given segment of the so determined tooth trajectory could be predetermined such that a displacement of the reference point therealong would not cause damage, such as tearing, of the PDL. As a result, while the reference point moves along the given segment, the other points defined on the tooth axis along the PDL would displace at a shorter distance, which prevents applying excessive stress to the PDL in its entirety, thereby avoiding damage thereof.

Further, in some non-limiting embodiments of the present technology, increased efficiency of the orthodontic treatment can be attained by optimizing a number of segments in the tooth trajectory. More specifically, the number of segments of the tooth trajectory can be minimized by increasing respective lengths thereof such that a length of the longest segment does not exceed a predetermined safety threshold value indicative of a maximum displacement of the reference point not causing damage to the PDL. By doing so, the overall time for conducting the orthodontic treatment may be reduced allowing for greater efficiency thereof.

Orthodontic Treatment

With initial reference to FIG. 1, there is depicted a perspective view of a lower arch form 10 of the subject (not depicted), to which certain aspects and non-limiting embodiments of the present technology may be applied.

As can be appreciated, the lower arch form 10 includes lower teeth 11 and a lower gingiva 13. Further, in the depicted embodiments of FIG. 1, current positions of at least some of the lower teeth 11 within the lower arch form 10 may be indicative of certain orthodontic disorders of the subject. For example, at least a given tooth 15 is misaligned within the lower gingiva 13 of the lower arch form 10.

Other malocclusions (not depicted) associated with misalignment of lower teeth 11, according to certain non-limiting embodiments of the present technology, may include, without limitation: overbites, underbites, crossbites, openbites, crowding of some of the lower teeth 11, excess spaces therebetween, shift of a midline thereof relative to upper teeth (not depicted) of the subject, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance to the subject's teeth. Generally speaking, the orthodontic appliance may be configured to exert a respective predetermined force onto at least some of the lower teeth 11 such as, for example, the given tooth 15, causing them to move towards an aligned position, thereby restoring the normal occlusion within the lower teeth 11 of the subject. More specifically, in the depicted embodiments of FIG. 1, the orthodontic appliance may be configured to cause the given tooth 15 to move inwardly between its adjacent teeth within the lower arch form 10; and further cause extrusion thereof, that is, displacement of the given tooth 15 out of its socket in the lower gingiva 14. In various non-limiting embodiments of the present technology, the orthodontic appliance may comprise orthodontic appliances of different types, shapes, sizes and configurations, such as those including, without limitation, aligners, brackets, multistrand wires, strips, retainers, and plates.

Figure 2A:
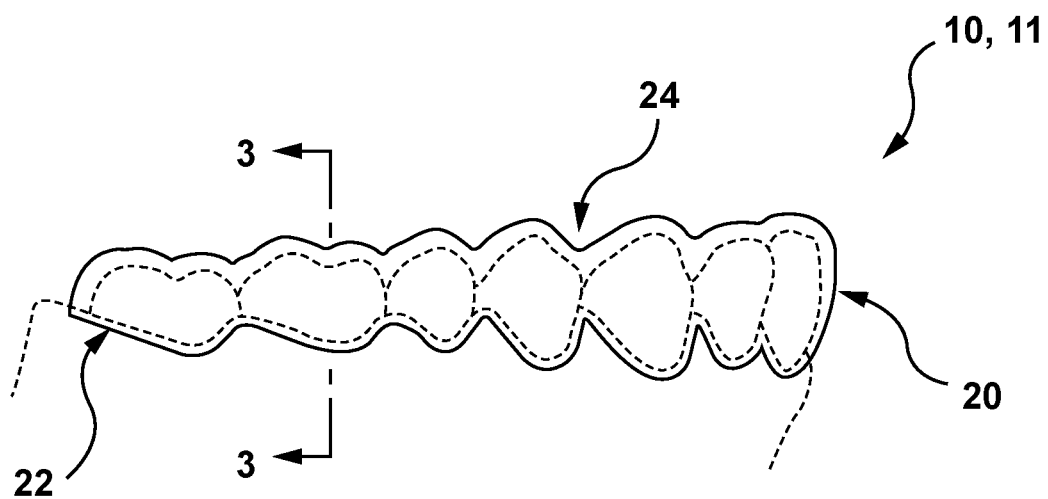
FIGS. 2A and 2B depict a side view and a cross-sectional view through line 3-3, respectively, of a dental appliance applied to the subject's teeth that may be configured to treat the malocclusions of the subject's teeth present in FIG. 1, in accordance with certain non-limiting embodiments of the present technology.
Figure 2B:
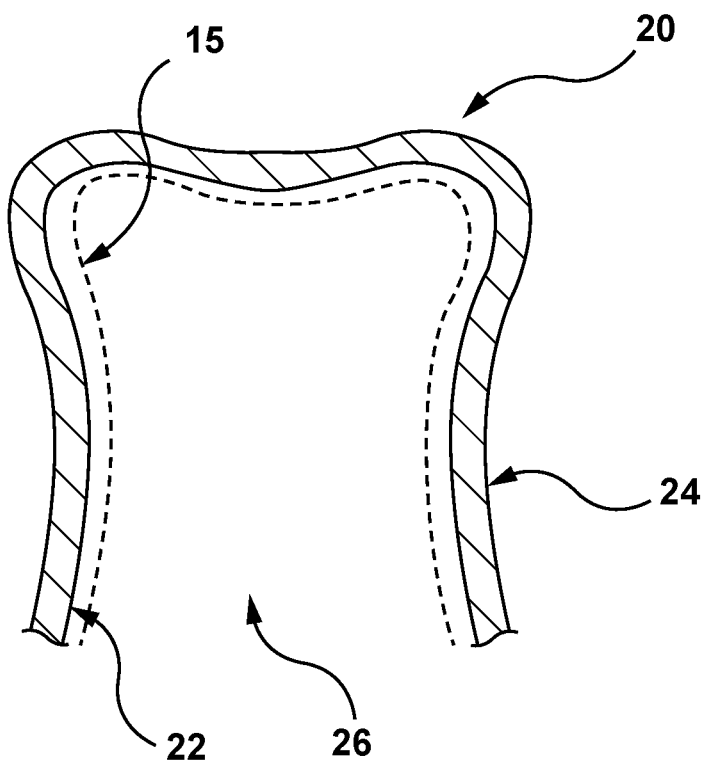

In specific non-limiting embodiments of the present the present technology, the orthodontic appliance may include at least one aligner applied to the lower teeth 11. With reference to FIGS. 2A and 2B, there is depicted an aligner 20 applied to at least some of the lower teeth 11, in accordance with certain non-limiting embodiments of the present technology. The aligner 20 comprises an inner surface 22 and an outer surface 24. The inner surface 22 defines a channel 26, which is configured, in some non-limiting embodiments of the present technology, for receiving crown portions of at least some of the lower teeth 11, such as the given tooth 15. However, in other non-limiting embodiments of the present technology, the channel 26 of the aligner 20 may be configured to receive crown portions of all of the lower teeth 11. At least one edge (also referred to herein as an "open edge") of the channel 26 is shaped for following a gum line (not depicted) along the lower gingiva 13.

It will be appreciated that, in accordance with certain non-limiting embodiments of the present technology, the aligner 20 may be configured to cause different movements to the at least some of the lower teeth 11 in order to treat malocclusions associated therewith, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 20 to the lower teeth 11 may further include applying specific attachments thereto.

As may become apparent, the aligner 20 may be designed in such a way that its inner surface 22 is configured to impose respective forces on one or more of the lower teeth 11 to obtain a desired position of the lower teeth 11 at a given stage of the orthodontic treatment.

Needles to say that, although in the depicted embodiments of FIGS. 2A and 2B, the aligner 20 is configured to be applied onto the lower teeth 11, in other non-limiting embodiments of the present technology, a respective configuration of the aligner 20 may be applied to the upper teeth (not depicted) of the subject for treating misalignment of at least some thereof. By so doing, the desired occlusion within the lower teeth 11 as well as between the lower teeth and the upper teeth (not depicted) may be attained.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D digital model thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 22 of the aligner 20; and (2) the unfinished aligner is cut along a predetermined cut line to remove excess material therefrom, thereby producing the aligner 20, the predetermined cut line defining the at least one edge of the channel 26 of the aligner 20.

In specific non-limiting embodiments of the present technology, the aligner 20 may be manufactured in accordance with one or more methods described in a co-owned U.S. Pat. No. 11,191,618-B1, issued on Dec. 7, 2021, entitled "SYSTEMS AND METHODS FOR FORMING A DENTAL APPLIANCE," the content of which is incorporated herein by reference in its entirety.

As it may become apparent, to produce the aligner 20 for achieving the desired occlusion of the lower teeth 11 during the orthodontic treatment, the tooth movements of those of the lower teeth 11, such as the given tooth 15, to which the aligner 20 is to be applied to should be carefully planned. More specifically, a tooth trajectory of the given tooth 15 defining a path thereof from its current position to its target position (such as the aligned position, for example) should be determined.

For example, in certain non-limiting embodiments of the present technology, the tooth trajectory can be determined using a respective 3D digital model (such as 3D meshes, as will be described below) of the lower arch form 10 including at least a 3D digital model of the given tooth 15. For example, the respective 3D digital model of the lower arch form 10 of the subject may be generated using intra-oral scanning techniques.

In some non-limiting embodiments of the present technology, to determine the tooth trajectory of the given tooth, a reference point within the given tooth 15, representative of the overall movement thereof in the course of the orthodontic treatment, should be determined. Broadly speaking, once the reference point has been determined, the tooth trajectory of the given tooth 15 can be constructed as a trajectory of the reference point as the given tooth 15 moves from the current position to the target position thereof. Further, at least one configuration of the aligner 20 can be produced and applied to the lower teeth 11 of the subject to cause movement of the given tooth 15 along a given segment of the plurality of segments towards the target position of the given tooth 15.

Figure 3:
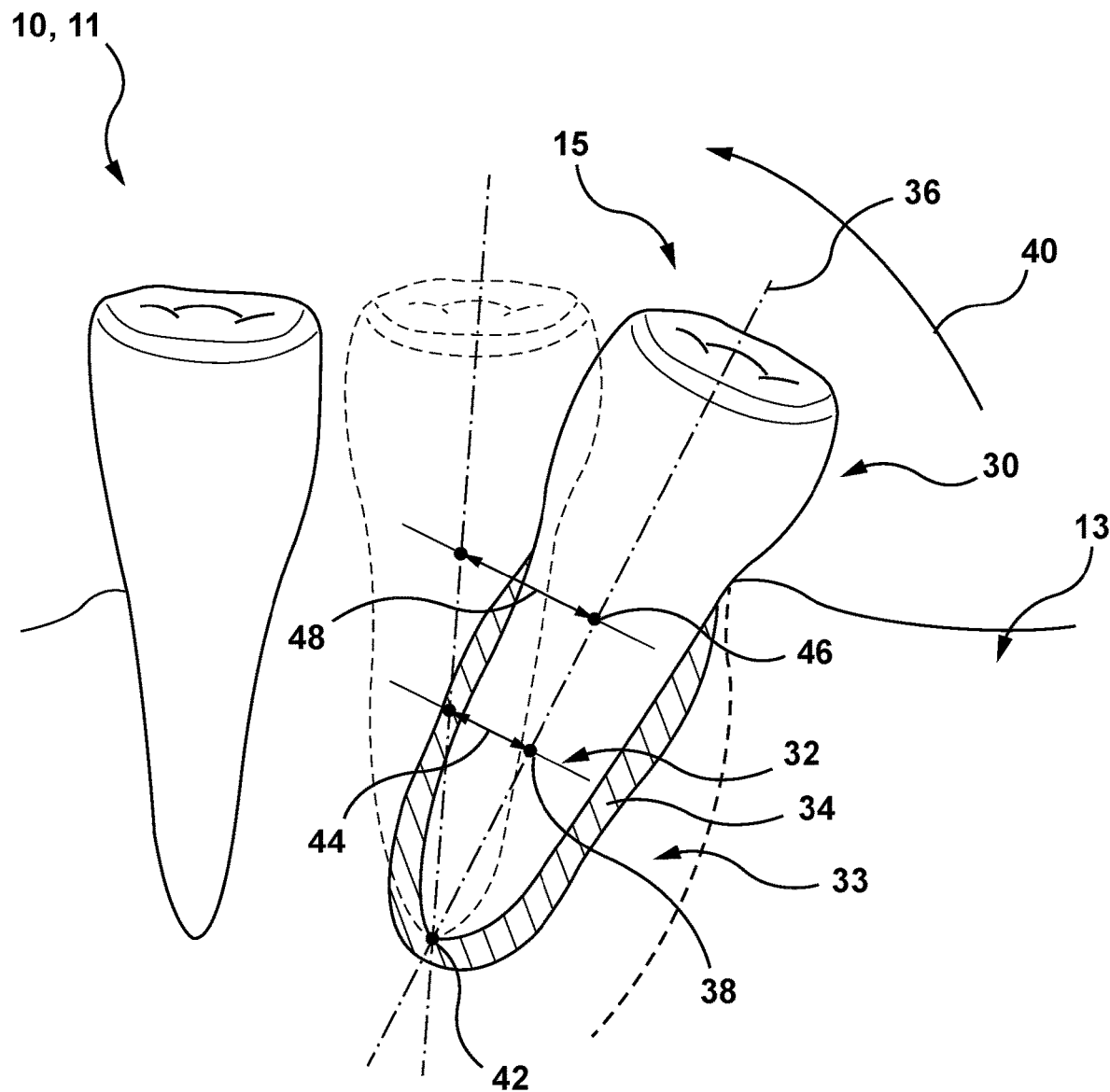
FIG. 3 depicts a schematic diagram of modelling a tooth movement of a given one of the subject's teeth present in FIG. 1, in accordance with certain embodiments of the present technology.

With reference to FIG. 3, there is depicted a coronal section of the given tooth 15 observed from the mesial aspect illustrating a process of modelling a given movement of the given tooth 15 in the course of the orthodontic treatment, in accordance with certain non-limiting embodiments of the present technology.

As it can be appreciated, the given tooth 15 includes a crown portion 30 and a root portion 32. Tissues of a periodontium surrounding and supporting the lower teeth 11, and the given tooth 15, in particular, include the gingiva 13, an alveolar bone 33, and a periodontal ligament (PDL) 34. The PDL 34 surrounds the root portion 32 and attaches the given tooth 15 to the alveolar bone 33. Thus, it can be said that the given tooth 15 is restrained in the alveolar bone 33 by forces (not separately depicted) from the PDL 34 and neighboring ones of the lower teeth 11 (depicted in FIGS. 1 and 2).

For example, in its current position (depicted in bold lines in FIG. 3), the given tooth 15 is misaligned relative to an adjacent one of the lower teeth 1. More specifically, the given tooth 15 is positioned such that the crown portion 30 thereof is inclined buccally while the root portion 32 is directed lingually. Thus, to correct the misalignment, it can be planned to cause the given tooth 15 to perform a tipping movement about an apex 42 of the root portion 32, in a direction 40, towards the target position of the given tooth 15 (depicted in dashed lines in FIG. 3), which may be associated with the alignment of the given tooth 15 within the lower arch form 10.

Thus, a tooth trajectory of such a movement may need to be determined. For example, the tooth trajectory can be determined as a trajectory of a center of resistance (CR) point 38 of the given tooth 15. Broadly speaking, the CR point 38 can be considered as an equivalent to a center of gravity point (center of mass point) for unrestrained (free) bodies. A location of the CR point 38 within the given tooth 15 may vary depending on a number of roots of the root portion 32, a length of the root portion 32, and a level (height) of the alveolar bone 33. However, generally, the location of the CR point 38 can be determined on a tooth axis 36 of the given tooth 15 at around ¼ to ⅓ of a distance between a cementoenamel junction (not depicted) of the given tooth 15 and the apex 42.

Thus, having determined the CR point 38, the tooth trajectory can be determined by joining instances of the CR point 38 in the current and target positions of the given tooth 15, for example, by a line segment, such as a first reference line 44. Further, the first reference line 44 can be segmented into a plurality of segments, thereby defining a number of steps of the orthodontic treatment to cause the given tooth 15 to move to the target position. Further, a respective configuration of the aligner 20 can be produced exerting a necessary force onto the given tooth 15 to cause the CR point 38 to move along a given segment of the first reference line 44.

For example, segmenting the first reference line 44 can be executed taking into account safety requirements associated with the PDL 34. More specifically, a length of a given segment of the plurality of segments can be determined not to exceed a predetermined safety distance threshold. Broadly speaking, if the CR point 38 is caused to displace at a distance greater than the predetermined safety distance threshold, the PDL 34 can be damaged, such as torn, which may cause pain to the subject or even have certain long-term side effects, such as resorption of the root portion 32 or that of the alveolar bone 33, as an example. For example, in some non-limiting embodiments of the present technology, the predetermined safety distance threshold can be determined to be from around 0.2 mm to around 0.3 mm.

However, even if each one of the plurality of segments of the first reference line 44 does not exceed the predetermined safety distance threshold, the PDL 34 can still be damaged if the tooth movements are planned based on the CR point 38 only. For example, as it can further be appreciated from FIG. 3, as the given tooth 15 tips about the apex 42, the CR point 38 is moving along the given segment of the first reference line 44; at the same time, a given point 46 lying on the tooth axis 36 within the crown portion 30 may move along a longer respective segment of a second reference line 48 which may exceed the predetermined safety distance threshold causing damage to the PDL 34.

Thus, certain non-limiting embodiments of the present technology are directed to determining the reference point, which may or may not be the CR point 38, for determining the tooth trajectory for the given tooth 15 as a point on the tooth axis 36 corresponding to one of vertical boundaries of the PDL 34, that is, at one of the crown portion 30 and the root portion 32. To that end, first, the methods and systems described herein are directed to determining a crown reference point indicative of a boundary of the PDL 34 at the crown portion 30 and a root reference point indicative of a boundary of the PDL 34 at the root portion 32. Second, based on the crown reference point, the root reference point, and an indication of the target position of the given tooth, a crown trajectory defining a movement of the crown reference point and a root trajectory defining a movement of the root reference point can be determined. Further, according to certain non-limiting embodiments of the present technology, a longer one of the crown trajectory and the root trajectory can be selected for further determining the number of steps of the orthodontic treatment. The respective configurations of the aligner 20 to be applied to the given tooth 15 could thus be configured to cause movement of the so determined reference point associated with the longer trajectory.

Additionally, the present methods and systems can be directed to minimizing the number of segments into which the longer trajectory of one of the reference points is to be segmented based on the predetermined safety distance threshold, which may help reduce a total number of respective configurations of the aligner 20 used for causing the given tooth 15 to reach the target position, thereby reducing the overall time of the orthodontic treatment.

Thus, the damage to the PDL 34 can be minimized (or even prevented/avoided) as no other point lying on the tooth axis 36 between the crown reference point and the root reference point representative of the boundaries of the PDL 34 would move at a longer distance in a given step of the orthodontic treatment than that thereof which is associated with the longer trajectory.

How the crown reference point and the root reference point can be determined, according to certain non-limiting embodiments of the present technology, will be described in detail below with reference to FIGS. 7 to 9. How the crown trajectory and the root trajectory can be determined, in accordance with certain non-limiting embodiments of the present technology, will be described further below with reference to FIG. 10.

System

Figure 4:
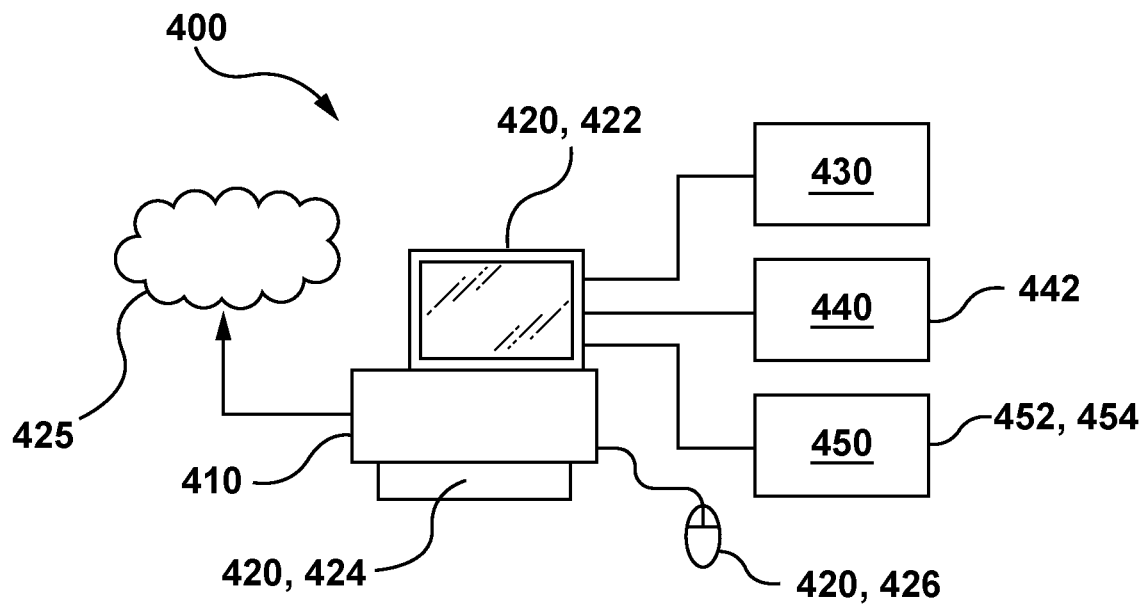
FIG. 4 depicts a schematic diagram of a computer system for determining an orthodontic treatment, in accordance with certain non-limiting embodiments of the present technology.
Figure 5:
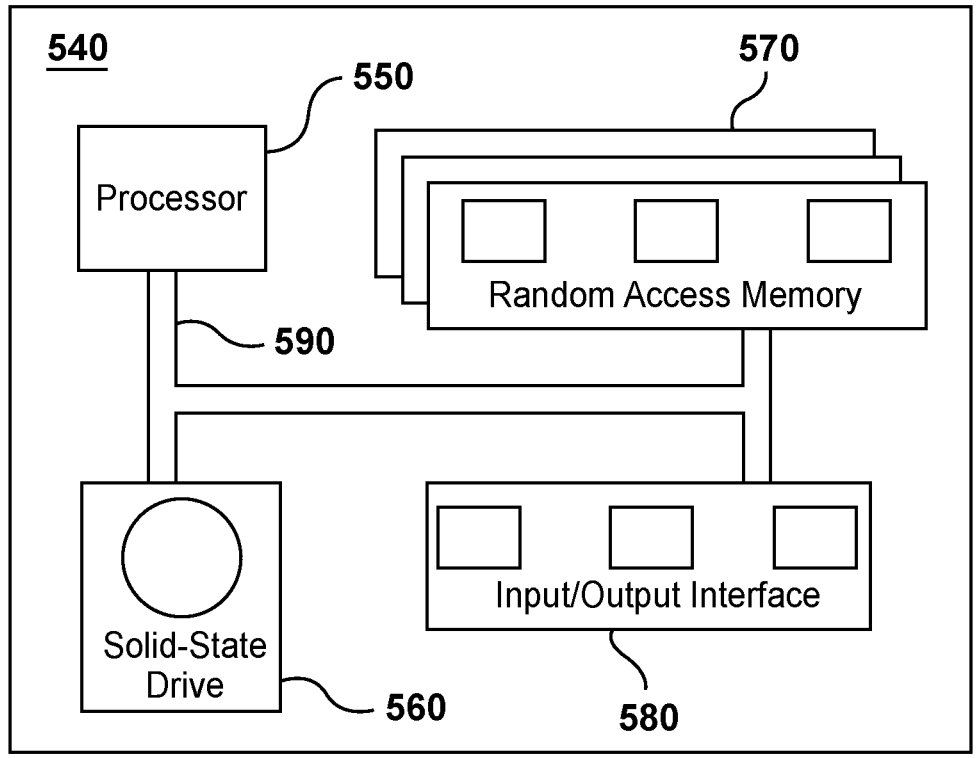
FIG. 5 depicts a schematic diagram of a computing environment of the system of FIG. 4, in accordance with certain embodiments of the present technology.

With reference to FIGS. 4 and 5, there is depicted a schematic diagram of a system 400 suitable for planning the orthodontic treatment for the given tooth 15 of the subject based on determining the tooth trajectory of the given tooth 15, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to determine, based on image data associated with the subject, such as the respective 3D digital model of the lower arch form 10, the tooth trajectory of the given tooth 15, and further using the data of the tooth trajectory for planning the orthodontic treatment, such as that using the aligner 20 as described above. In additional non-limiting embodiments of the present technology, the computer system 410 may further be configured to produce at least one configuration of the aligner 20 based on the so planned orthodontic treatment.

To that end, in some non-limiting embodiments of the present technology, the computer system 410 may be configured to receive image data pertaining to the subject or to a given stage of the orthodontic treatment. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (for example, such as the crown portion 30 of the given tooth 15) extending outwardly of the gingival sulcus. In some embodiments, the image data is indicative of properties of internal portions of the anatomical structures, for example volumetric properties of bone surrounding an internal portion of the tooth (for example, the root portion 32 of the given tooth 15) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

Further, as noted above, after the determining the tooth trajectory for the given tooth 15, in some non-limiting embodiments of the present technology, the system 400 may be configured, based the respective 3D digital model of the lower arch form 10, determine the orthodontic treatment for the subject including forces to be applied onto the given tooth 15 to cause the given tooth 15 to move to the target position thereof. In specific non-limiting embodiments of the present technology, the orthodontic treatment may be determined (for example, by a processor 550 depicted in FIG. 5) as described in a co-owned U.S. Pat. No. 10,993,782-B1 issued on May 4, 2021, and entitled "SYSTEMS AND METHODS FOR DETERMINING A TOOTH TRAJECTORY"; a content of which is hereby incorporated by reference in its entirety.

In alternative non-limiting embodiments of the present technology, the computer system 410 may be configured to receive the image data associated with the subject directly from an imaging device 430 communicatively coupled thereto. Broadly speaking, the processor 550 may be configured to cause the imaging device 430 to capture and/or process the image data of the lower teeth 11 and the periodontium (not depicted) of the subject. In certain non-limiting embodiments of the present technology, the image data may include, for example, one or more of: (1) images of external surfaces of respective crown portions of the lower teeth 11, (2) images of an external surface of the periodontium including those of the lower gingiva 13, the alveolar mandibular bone (not depicted), and images of superficial blood vessels and nerve pathways associated with the lower teeth 11; and (3) images of an oral region. By doing so, the imaging device 430 may be configured, for example, to capture image data of the lower arch form 10 of the subject. In another example, the imaging device may also be configured to capture and/or process image data of an upper arch form (not depicted) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of the lower arch form 10 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In yet other non-limiting embodiments of the present technology, the imaging device 430 can comprise a 3D laser scanner enabling to obtain a respective point cloud 3D digital model of the lower arch form 10— such as by scanning a mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, MN 55416. It should be expressly understood that the desktop scanner can be implemented in any other suitable equipment.

In yet other non-limiting embodiments of the present technology, the imaging device 430 may comprise a cone beam computed tomography (CBCT) scanner. Generally speaking, the CBCT scanner comprises software and hardware allowing for capturing data using a cone-shaped X-ray beam by rotating around the subject's head. This data may be used to reconstruct 3D digital models of the following regions of the subject's anatomy: dental (teeth and gum, for example); oral and maxillofacial region (mouth, jaws, and neck); and ears, nose, and throat ("ENT").

In a specific non-limiting example, the CBCT scanner can be of one of the types available from 3SHAPE, PRIVATE LIMITED COMPANY of Holmens Kanal 7, 1060 Copenhagen, Denmark. It should be expressly understood that the CBCT scanner can be implemented in any other suitable equipment.

Further, it is contemplated that the computer system 410 may be configured for processing of the received image data. The resulting image data of the lower arch form 10 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

Further, in certain non-limiting embodiments of the present technology, the system 400 may be configured to produced at least one configuration of the aligner 20 based on the planned orthodontic treatment as mentioned above. For example, in certain non-limiting embodiments of the present technology, the system 400 can be configured to produce an unfinished aligner (not depicted), for example, using a thermopriming process, in which a preform aligner (not depicted) is shaped on the mold of the lower arch form 10. Further, the system 400 can be configured to trim excess material along a cut line to produce an edge of the aligner 20.

Thus, in some non-limiting embodiments of the present technology, the system 400 can be configured to receive data indicative of the cut line and mark the curt line on the unfinished aligner. To that end, the system 400 may further comprise a marking subsystem 440. It is not limited how the marking subsystem 440 may be implemented; however, in various non-limiting embodiments of the present technology, the marking subsystem 440 may include a marking head 442 for applying the cut line onto the unfinished aligner and a first robotic arm (not depicted) for holding and manipulating the unfinished aligner (not depicted) around the marking head 442. In some non-limiting embodiments of the present technology, the marking head 442 may further comprise a coloring material storage (not depicted) for storing a coloring material (such as ink, as an example) and a supply control block (not depicted). In some non-limiting embodiments of the present technology, the marking head 442 may be implemented as a laser apparatus configurable to scorch the cut line (not depicted) on the unfinished aligner (not depicted).

In certain non-limiting embodiments of the present technology, the system 400 may further be configured to detect the cut line applied on the unfinished aligner and cut along the cut line to produce the aligner 20. In this regard, the system 400 may further comprise a forming subsystem 450. In some non-limiting embodiments of the present technology, the forming subsystem 450 may include a second robotic arm (not depicted), at an end-effector of which there is installed a camera device 452. In some non-limiting embodiments of the present technology, the camera device 452 can be any appropriate digital camera configured to detect the cut line applied by the marking subsystem 440 described above onto the unfinished aligner, including, for example, but not limited to, a coupled-charged device camera (a CCD camera). Further, as mentioned above, the forming subsystem 450 may include the cutting device 454. Non limiting examples of the cutting device 454 may include a laser-based cutting device, a mechanical cutting device such as using a blade with a rotary or linear cutting action, and a water-jet based cutting device, as an example.

In some non-limiting embodiments of the present technology, both the marking subsystem 440 and the forming subsystem 450 of the system 400 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety.

Thus, the forming subsystem 450 may be configured to: (1) cause the camera device 452 to move around the unfinished aligner (not depicted) with the cut line (not depicted) applied thereon to detect the cut line and generating respective image data thereof; (2) receive the image data of the cut line; and (3) based on the received image data of the cut line, cause cutting, by the cutting device 454 the unfinished aligner along the cut line, thereby forming the aligner 20.

In other non-limiting embodiments of the present technology, the forming subsystem 450 may be configured for cutting the unfinished aligner without requiring detection of the cut line. Instead, the determined cut line is used to guide the cutting—for example, based on received data indicative of a position of the cut line within the unfinished aligner. In some non-limiting embodiments of the present technology, the data indicative of the position of the cut line 304 within the unfinished aligner may include at least one of: Cartesian coordinates; angular data indicative of a cutting angle for cutting the unfinished aligner; and a distance from the cutting device 454, as an example.

Further, with reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random-access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet", Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as IP.

According to implementations of the present technology, the solid-state drive 560 stores program instructions suitable for being loaded into the random-access memory 570 and executed by the processor 550, according to certain aspects and embodiments of the present technology. For example, the program instructions may be part of a library or an application.

In some non-limiting embodiments of the present technology, the computing environment 540 is implemented in a generic computer system, which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As alluded to above, according to certain non-limiting embodiments of the present technology, the processor 550 may be configured to: (1) receive the respective 3D digital model of the given configuration of the lower arch form 10 including the 3D digital model of the given tooth; (2) determine, based on the respective 3D digital model, the tooth trajectory of the given tooth 15; and (3) based on the tooth trajectory, determine the orthodontic treatment for the subject.

Figure 6:
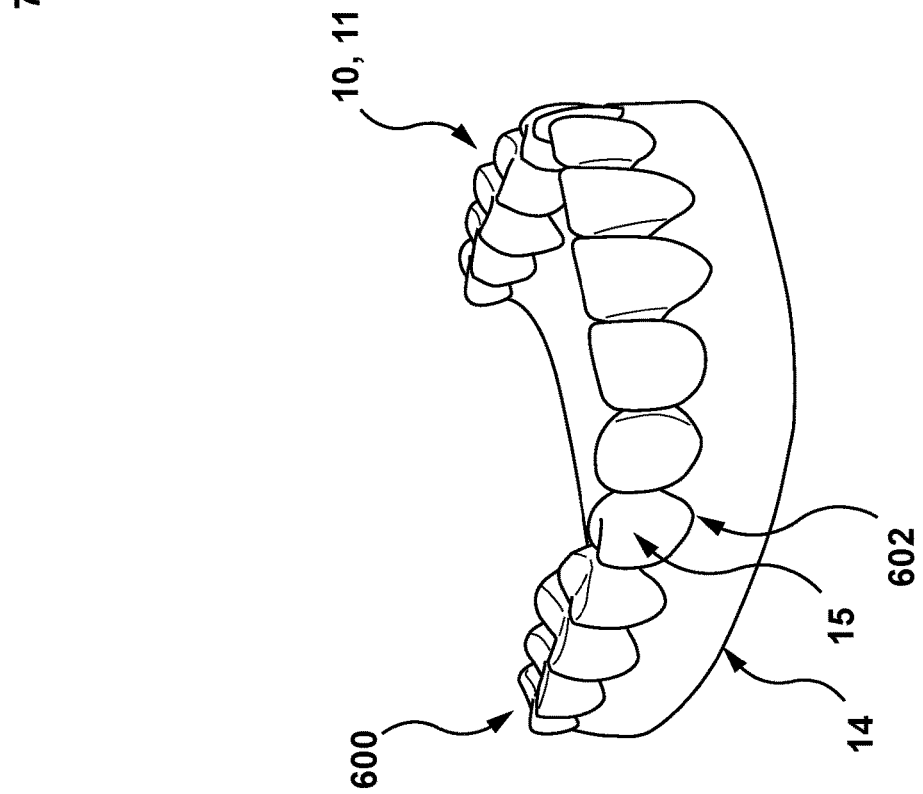
FIG. 6 depicts a 3D digital model of the lower arch form of the subject present in FIG. 1 used, by a processor of FIG. 5, to determine a tooth trajectory of a given tooth of the subject during the orthodontic treatment, in accordance with certain non-limiting embodiments of the present technology.

With reference to FIG. 6, there is schematically depicted a perspective view of an arch form 3D digital model 600 of the lower arch form 10 used, by the processor 550, for determining the tooth trajectory of the given tooth 15, in accordance with certain non-limiting embodiments of the present technology.

In some non-limiting embodiments of the present technology, the processor 550 may be configured to receive, from the imaging device 430, the arch form 3D digital model 600 comprising a respective plurality of mesh elements (not depicted) representative of a surface of the lower arch form 10. For example, the imaging device 430 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

As noted above, according to the non-limiting embodiments of the present technology, the lower arch form 10 comprises the lower teeth 11 (also referred to herein as "mandibular teeth") and the lower gingiva 13. As it can be appreciated, the lower teeth 11 are represented, in the arch form 3D model 600, by respective crown portions associated therewith, such as the crown portion 30 of the given tooth 15.

It should be expressly understood that, although the description herein below will be given in respect of the lower arch form 10 of the subject (and associated therewith the lower teeth 11 and the lower gingiva 13) for the sake of clarity and simplicity thereof, and in no way as a limitation, the non-limiting embodiments of the present technology can also apply to the upper teeth (not depicted) of the subject with certain alterations, which will be explicitly indicated below where necessary.

Further, according to certain non-limiting embodiments of the present technology, based on the arch form 3D digital model 600, the processor 550 can be configured to generate a 3D digital model of the given tooth 15. With continued reference to FIG. 6 and with reference to FIG. 7, there is depicted a schematic diagram of a tooth 3D digital model 700 of the given tooth 15, in accordance with certain non-limiting embodiments of the present technology.

In some non-limiting embodiments of the present technology, to generate the tooth 3D digital model 700, the processor 550 can be configured to (1) isolate, within the arch form 3D digital model 600, a crown 3D digital model 702 of the crown portion 30 of the given tooth 15 from adjacent teeth and the lower gingiva 13; (2) based on crown the 3D digital model 702 of the crown portion 30, reconstruct a root 3D digital model 704 of the root portion 32 of the given tooth 15; and (3) merge the crown 3D digital model 702 and the root 3D digital model 704.

How the processor 550 can be configured to isolate the crown 3D digital model 702 is not limited; and, in some non-limiting embodiments of the present technology, the processor 550 can be configured to apply, to the arch form 3D digital model 600, one or more automatic tooth segmentation approaches described in a co-owned U.S. Pat. No. 10,950,061-B1 issued on Mar. 16, 2021, entitled "SYSTEMS AND METHODS FOR PLANNING AN ORTHODONTIC TREATMENT", content of which is incorporated herein by reference in its entirety.

More specifically, to generate the crown 3D digital model 702 associated with the given tooth 15, the processor 550 may be configured to: (i) acquire the arch form 3D digital model 600 of the lower arch form 10 of the subject, the arch form 3D digital model 600 comprising a defined portion forming part of a surface of the given tooth 15, and at least one undefined portion not forming part of the surface of the given tooth 15; the arch form 3D digital model 600 comprising the plurality of mesh elements having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; (ii) generate a set of confirmed constrained vertices, including the constrained vertices associated with the defined portion, for providing the crown 3D digital model 702 of the crown portion of the given tooth 15 by: (iii) iteratively, for a given constrained vertex, identifying at least one associated unconstrained vertex which is adjacent to the given constrained vertex in the plurality of mesh elements; (iv) determining an angular difference between the normal constrained vertex vector of the given constrained vertex and the normal unconstrained vertex vector of the at least one associated unconstrained vertex; (v) in response to the angular difference being equal to or below a predetermined threshold value: identifying the at least one associated unconstrained vertex to be a constrained vertex associated with the defined portion for inclusion in the set of confirmed constrained vertices; (vi) in response to the angular difference being above the predetermined threshold value: identifying the at least one associated unconstrained vertex to be an unconstrained vertex associated with the undefined portion for exclusion from the set of confirmed constrained vertices.

Further, as noted above, the processor 550 may be configured to generate the root 3D digital model 704 of the root portion 32 based on the crown 3D digital model 702. It is not limited how the processor 550 may be configured to generate the root 3D digital model 704 of the root portion 32; however, in some non-limiting embodiments of the present technology, the processor 550 may be configured to generate the root 3D digital model 704 of the root portion 32 based on reference data associated with the given tooth 15 applying one or more approaches described in a co-owned U.S. Pat. No. 11,026,767-B1 issued on Jun. 8, 2021, entitled "SYSTEMS AND METHODS FOR PLANNING AN ORTHODONTIC TREATMENT", content of which is incorporated herein by reference in its entirety.

More specifically, in some non-limiting embodiments of the present technology, the reference data associated with the given tooth 15 may include, without limitation, at least one of a number of root branches of the root portion; approximate overall dimensions of the given tooth 15 including those of the crown portion 30 and the root portion 32 thereof. Also, in some non-limiting embodiments of the present technology, the reference data associated with the given tooth 15 may further include a base parametric 3D model of the root portion 32; and the processor 550 can be configured to generate the root 3D digital model 704 of the root portion 32 of the given tooth 15 based on the base parametric 3D model.

Thus, having generated the root 3D digital model 704, in some non-limiting embodiments of the present technology, the processor 550 may be configured to merge it with the crown 3D digital model 702 to generate the tooth 3D digital model 700 of the given tooth 15.

Alternatively, in those non-limiting embodiments of the present technology where the imaging device 430 is a CBCT scanner, the processor 550 can be configured to receive the tooth 3D digital model 700 directly from the imaging device 430 or isolate it within the arch form 3D digital model 600 without having to restore the root 3D digital model 704 therefrom.

Further, as noted above, the processor 550 can be configured to determine the orthodontic treatment based on analyzing trajectories of each one of the crown portion 30 and the root portion 32. Thus, according to certain non-limiting embodiments of the present technology, the processor can be configured to determine, based on the arch form 3D digital model 600 of the lower arch form 10, a tooth-gingiva segmentation loop 602 indicative of a boundary between the crown portion 30 of the given tooth 15 and the lower gingiva 13.

In some non-limiting embodiments of the present technology, the processor 550 can be configured to determine the tooth-gingiva segmentation loop 602 as a closed curve extending along an edge of the crown 3D digital model 702 generated as described above with reference to FIG. 7.

In other non-limiting embodiments of the present technology, the processor 550 may be configured to obtain the tooth-gingiva segmentation loop 602 having been previously generated by third-party software, based on the arch form 3D digital model 600, and data indicative thereof may have been stored in a data format, in which the processor 550 may be configured to receive it, for example, via the input/output interface 580.

In yet other non-limiting embodiments of the present technology, the tooth-gingiva segmentation loop 602 may be generated manually, for example, by a practicing clinician involved in the determining the orthodontic treatment. For example, a practicing clinician involved in the determining the orthodontic treatment for the subject may manually apply the tooth-gingiva segmentation loop 602 onto the arch form 3D digital model 600, using respective suitable software, and the processor 550 may further be configured to receive the arch form 3D digital model 600, and detect the tooth-gingiva segmentation loop 602 applied thereon.

Further, as will become apparent from the description provided hereinbelow, certain non-limiting embodiments of the present technology are based on a premise that reference points defining respective trajectories of the crown portion 30 and the root portion 32 of the given tooth 15 are lying therewithin, such as on a predetermined longitudinal axis 706 extending through the given tooth 15. In some non-limiting embodiments of the present technology, the predetermined longitudinal axis 706 may be predetermined, by the processor 550, based on data indicative of specific anatomical features of crown portion 30 which includes, without being limited to: lobes, developmental grooves, and marginal ridges, as an example. In these embodiments, the data indicative of the specific anatomical features of the crown portion 30 may be part of the reference data of the given tooth 15 and include data of spatial positions and dimensions of at least some of the above-listed anatomical features of the crown portion 30 averaged over the sample of subjects.

In specific non-limiting embodiments of the present technology, predetermined longitudinal axis 706 may be a central tooth axis associated with the given tooth 15, such as the tooth axis 36 depicted in FIG. 3, location of which the processor 550 can be configured to determine based on the crown 3D digital model 702 as described in a co-owned U.S. Pat. No. 10,856,954-B1 issued on Dec. 8, 2020 and entitled "SYSTEMS AND METHODS FOR DETERMINING TOOTH CENTER OF RESISTANCE", the content of which is hereby incorporated by reference in its entirety. More specifically, in these embodiments, the processor 550 can be configured to: (i) obtain the crown 3D digital model 702; (ii) identify an internal reference point within the crown 3D digital model 702, the internal reference point corresponding to a mesiodistal center of the crown portion 30, the identifying the internal reference point comprising: obtaining a mesial point on a mesial side of the crown portion 30, and a distal point on a distal side of the crown portion 30; generating a mesiodistal line joining the mesial point and the distal point; identifying the mesiodistal center as a midpoint on the mesiodistal line; (iii) determine a reference plane in the crown 3D digital model 702, the reference plane being perpendicular to the mesiodistal line and extending through the mesiodistal center; (iv) determine an intersection curve based on an intersection of the reference plane and the crown 3D digital model 702, the intersection curve following a shape of the surface of the crown 3D digital model 702 at the reference plane; and (v) determine the predetermined longitudinal axis 706 of the given tooth 15 based on the intersection curve.

Thus, having generated the tooth 3D digital model 700 of the given tooth 15, determined therein the tooth-gingiva segmentation loop 602, and identified the predetermined longitudinal axis 706, the processor 550 can be configured to plan the orthodontic treatment for the given tooth 15 by determining the tooth trajectory.

Further, in accordance with certain non-limiting embodiments of the present technology, based on the above data, the processor 550 can be configured to determine, in the current position of the given tooth 15, on the predetermined longitudinal axis 706, (i) a crown reference point 710 corresponding to a first vertical boundary of the PDL 34 of the given tooth 15 at the crown portion 30; (ii) and a root reference point 712 corresponding to a second vertical boundary of the PDL 34 of the given tooth at the root portion 32. Further, the processor 550 can be configured to receive an indication of the target position of the given tooth 15, such as that depicted in FIG. 3. For example, in some non-limiting embodiments of the present technology, the target position may be provided by the practicing clinician involved in the determining the orthodontic treatment for the subject. However, in other non-limiting embodiments of the present technology, the target position can be determined by the processor determining, based on the arch form 3D digital model 600, a tooth movement of the given tooth 15 required to place it in alignment within other ones of the lower teeth 11.

Thus, based on the target position, the processor 550 can further be configured to trace movements of each one of the crown reference point 710 and the root reference point 712 from their respective current positions to their respective target positions, thereby determining a crown trajectory of the crown portion 30 and a root trajectory of the root portion 32. Further, according to certain non-limiting embodiments of the present technology, the processor 550 can be configured to determine the tooth trajectory of the given tooth 15 as one of the crown trajectory and the tooth trajectory.

How the processor 550 can be configured to determine the crown reference point 710 and the root reference point 712 as well as determine the tooth trajectory using such points, in accordance with certain non-limiting embodiments of the present technology, will now be described.

Determining Crown and Root Reference Points

According to certain non-limiting embodiments of the present technology, the processor 550 can be configured to determine the crown reference point 710 based on analyzing the tooth-gingiva segmentation loop 602.

Figure 8:
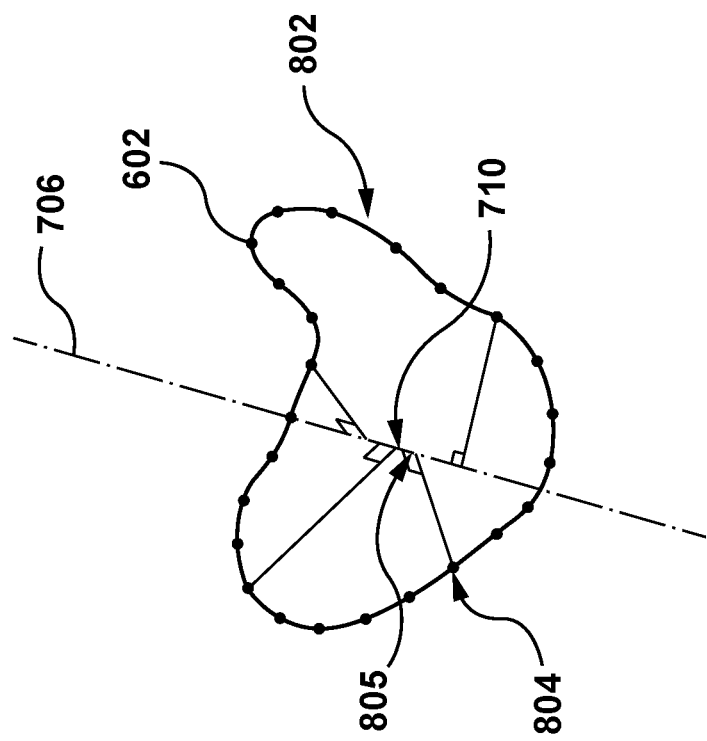
FIG. 8 depicts a schematic diagram of one approach to determining, by the processor of FIG. 5, a crown reference point for determining a crown trajectory of a crown portion of the given tooth in the course of the orthodontic treatment, according to certain embodiments of the present technology.

With reference to FIG. 8, there is depicted a schematic diagram of a step for determining the crown reference point 710, in accordance with certain non-limiting embodiments of the present technology.

According to certain non-limiting embodiments of the present technology, the processor 550 can be configured to determine the crown reference point 710 as a center of the tooth-gingiva segmentation loop 602 associated with the given tooth 15.

To that end, in some non-limiting embodiments of the present technology, the processor 550 can be configured to identify vertices 802 defining the tooth-gingiva segmentation loop 602. For example, the processor 550 can be configured to identify a given vertex 804 of the vertices 802. Further, the processor 550 can be configured to determine, over a respective normal vector, a projection 805 of the given vertex 804 on the predetermined longitudinal axis 706. By so doing, the processor 550 can be configured to determine the respective projections of each one of the vertices 802 onto the predetermined longitudinal axis 706.

In some non-limiting embodiments of the present technology, before determining the respective projections of each one of the vertices 802 onto the predetermined longitudinal axis 706, the processor 550 can be configured to redistribute the vertices 802 uniformly along the tooth-gingiva segmentation loop 602 based on a predetermined step, as an example.

Further, the processor 550 can be configured to determine the center of the tooth-gingiva segmentation loop 602 as a midpoint amongst the so determined projections of each one of the vertices 802 defining the tooth-gingiva segmentation loop 602. To that end, for example, the processor 550 can be configured to place the predetermined longitudinal axis 706 along a number-scale axis (not depicted), and determine the midpoint as a point having average coordinates amongst each one of the respective projections of the vertices 802.

In other non-limiting embodiments of the present technology, the processor 550 can be configured to determine the center of the tooth-gingiva segmentation loop 602, and thus the crown reference point 710, using a so-called bounding box around the tooth-gingiva segmentation loop 602. In the context of the present specification, the term "bounding box" is broadly referred to as a three-dimensional box (or a parallelepiped) of a smallest possible measure (such as an area or a volume thereof) allowing for entirely enclosing a given point set, such as the vertices 802 of the tooth-gingiva segmentation loop 602.

Figure 9:
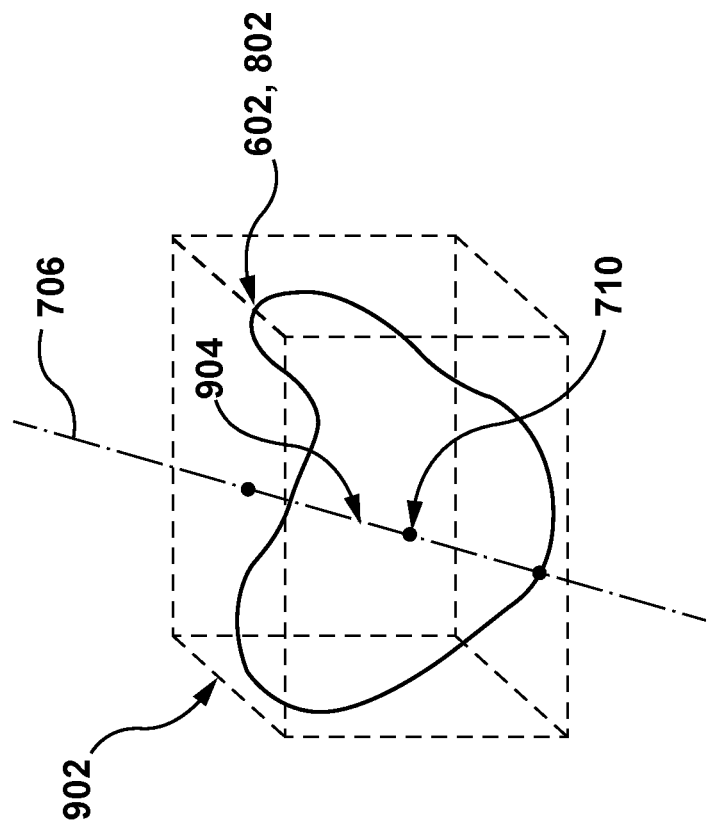
FIG. 9 depicts a schematic diagram of another approach to determining, by the processor of FIG. 5, the crown reference point, according to certain non-limiting embodiments of the present technology.

With reference to FIG. 9, there is depicted a schematic diagram illustrating another approach to determining the crown reference point 710 using a bounding box 902 generated around the tooth-gingiva segmentation loop 602, in accordance with certain non-limiting embodiments.

Thus, according to certain non-limiting embodiments of the present technology, the processor 550 can be configured to determine the center of the tooth-gingiva segmentation loop 602 as a midpoint of a segment 904 formed by intersection between the bounding box 902 and the predetermined longitudinal axis 706 associated with the given tooth 15.

Thus, the processor 550 can be configured to determine the crown reference point 710. In additional non-limiting embodiments of the present technology, the processor 550 can further be configured to offset the crown reference point 710 along the predetermined longitudinal axis 706 towards the root portion 32 at a crown offset predetermined distance. For example, the crown offset predetermined distance can be determined as an average distance between the tooth-gingiva segmentation loop 602 and a boundary of the PDL 34 at the crown portion 30 of the given tooth 15. In some non-limiting embodiments of the present technology, the crown offset predetermined distance can be provided as part of the reference data associated with the given tooth 15 as described above. However, in other non-limiting embodiments of the present technology, the crown offset predetermined distance can be determined empirically, based on data of a plurality of subjects, and comprise, for example, from around 0.2 mm to around 2 mm.

Further, referring back to FIG. 7, in some non-limiting embodiments of the present technology, the processor 550 can be configured to determine the root reference point 712 representative of the second boundary of the PDL 34 along the predetermined longitudinal axis as the apex 42 (depicted in FIG. 3) of the given tooth 15. For example, the processor 550 can be configured to determine a location of the apex 42 on the tooth 3D digital model 700 based on the reference data associated with the given tooth 15 used earlier for reconstructing the root portion 32 thereof. In other words, the processor 550 can be configured to determine the apex 42 based on approximate dimensions of the root portion 32 of the given tooth 15. It should be noted that in those embodiments where the root portion 32 has more than one root, based on the reference data, the processor 550 can be configured to determine the root reference point 712 as an apex of a longest root of the root portion 32.

Further, in some non-limiting embodiments of the present technology, the processor 550 can further be configured to offset the root reference point 712 along the predetermined longitudinal axis 706 at a root offset predetermined distance towards the crown portion 30. Similar to the crown offset predetermined distance, the root offset predetermined distance can be determined to correspond to a specific level of the PDL 34 of the given tooth 15 along the predetermined longitudinal axis 706 at the root portion 32. For example, the root offset predetermined distance can be determined such that the root reference point 712 corresponds to a level, along the predetermined longitudinal axis 706, at which the PDL 34 is thinnest (i.e. in a transverse direction to the longitudinal tooth axis). To that end, the root offset predetermined distance can comprise, for example, around ⅓ of a total length thereof along the predetermined longitudinal axis 706.

In other non-limiting embodiments of the present technology, the processor 550 can be configured to determine the root reference point 712 as being the CR point 38 as described above with reference to FIG. 3.

Determining the Tooth Trajectory

Figure 10:
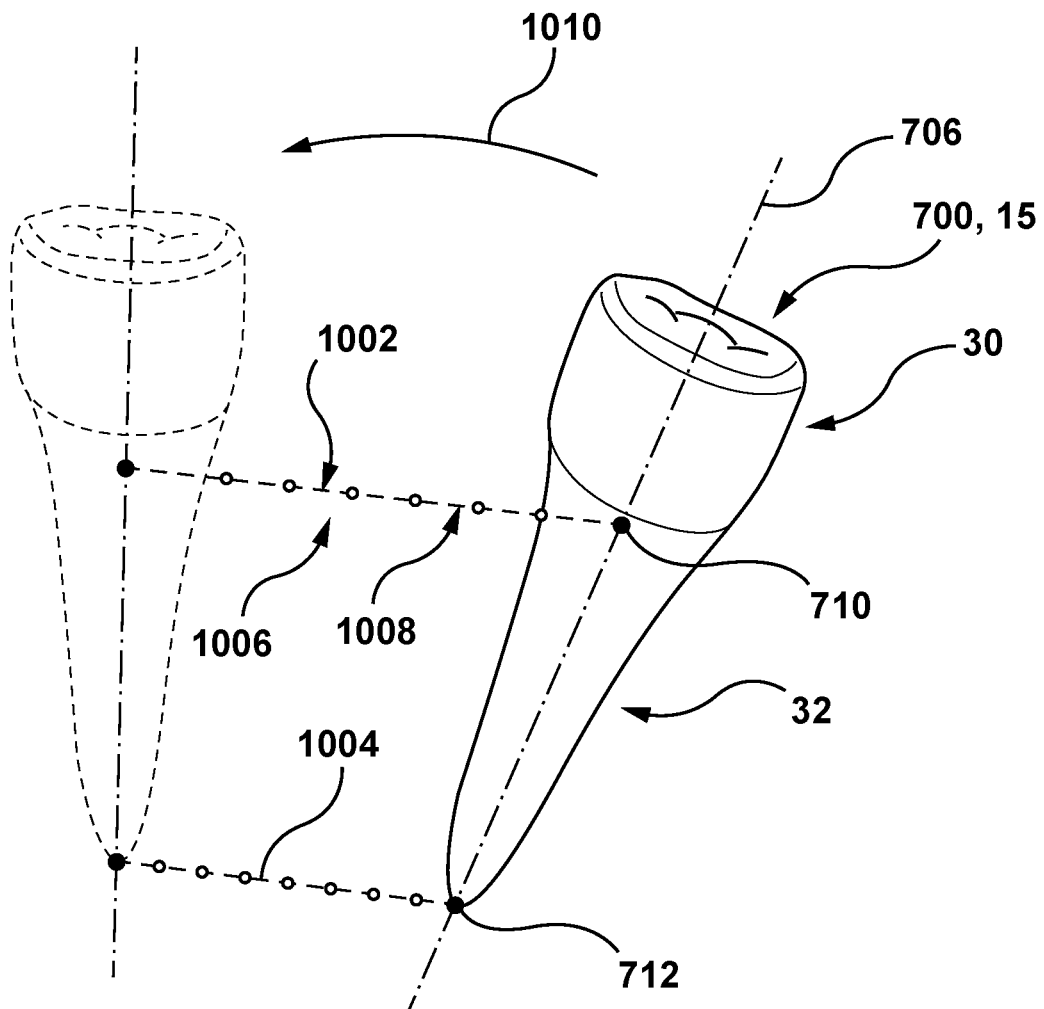
FIG. 10 depicts a schematic diagram of a process for determining, by the processor of FIG. 5, a crown trajectory of the crown portion and a root trajectory of a root portion of the given tooth, and, based thereon, determining the tooth trajectory for the given tooth, according to certain non-limiting embodiments of the present technology.

Having determined the crown reference point 710 and the root reference point 712, the processor 550 can be configured to determine the tooth trajectory of the given tooth 15. With reference to FIG. 10, there is depicted a schematic diagram of a step for determining the tooth trajectory, in accordance with certain non-limiting embodiments of the present technology.

As it can be appreciated form FIG. 10, the determining the tooth trajectory can be performed for a given tooth movement 1010 of the given tooth 15 in the course of the orthodontic treatment. According to certain non-limiting embodiments of the present technology, the given tooth movement 1010 may include at least one of the following types of orthodontic tooth movements, without limitation: uncontrolled tipping, controlled tipping, translational, uprighting, extrusion, and intrusion.

To that end, as mentioned above, when modelling the given tooth movement 1010, using the tooth 3D digital model 700, the processor 550 can be configured to receive (1) the current position (depicted in bold lines in FIG. 10) of the given tooth 15—such as that within the arch form 3D digital model 600 and (2) the target position (depicted in dashed lines in FIG. 10) of the given tooth 15, towards which the given tooth 15 is to be caused to move in the course of the orthodontic treatment.

Further, based on the current and target positions of the given tooth 15, according to certain non-limiting embodiments of the present technology, the processor 550 could be configured to join instances of the crown reference point 710 in the current and target positions of the given tooth 15, thereby defining a crown reference line 1002 representative of the crown trajectory of the crown portion 30 of the given tooth 15. Further, the processor 550 could be configured to join instances of the root reference point 712 in the current and the target positions of the given tooth 15, thereby defining a root reference line 1004 representative of the root trajectory of the root portion 32 of the given tooth 15.

It should be noted that although in the embodiments of FIG. 10, each one of the crown reference line 1002 and the root reference line 1004 are line segments, in other non-limiting embodiments of the present technology, depending on a particular type of the given tooth movement 1010, the processor 550 can be configured to join the instances of the crown reference point 710 and the root reference point 712 with lines of other curvatures, such as arcs, as an example.

Further, according to certain non-limiting embodiments of the present technology, the processor 550 can be configured to determine the tooth trajectory of the given tooth 15 as being a longer one of the crown reference line 1002 and the root reference line 1004, which is, in the example of FIG. 10, the crown reference line 1002.

However, in other non-limiting embodiments of the present technology, to determine the tooth trajectory of the given tooth 15, the processor 550 can be configured to consider a plurality of crown and root reference lines. To that end, in these embodiments, first, the processor 550 can be configured to (i) determine a plurality of crown reference points and a plurality of root reference points; (ii) based on the target position of the given tooth 15, for each one of the plurality of crown reference points, determine a respective target crown reference point, thereby defining a plurality of crown reference lines, each of which is similar to the crown reference line 1002; (iii) based on the target position of the given tooth 15, for each one of the plurality of root reference points, a respective target root reference point, thereby defining a plurality of root reference lines, each of which is similar to the root reference line 1004; (iii) determine, from each one of the plurality of crown reference lines and the plurality of root reference lines, a longest crown reference line and a longest root reference line as being representative of the crown and root trajectories of the given tooth 15, respectively; and (iv) determine the tooth trajectory of the given tooth 15 as being a longer one of the longest crown reference line and the longest root reference line, similarly to the approach described above with respect to the crown reference line 1002 and the root reference line 1004.

It is not limited how the processor 550 can be configured to obtain the plurality of crown reference points and the plurality of root reference points to generate the pluralities of crown and root reference lines. In some non-limiting embodiments of the present technology, the processor 550 can be configured to determine points around a respective one of the crown reference point 710 and the root reference point 712.

Figure 11B:
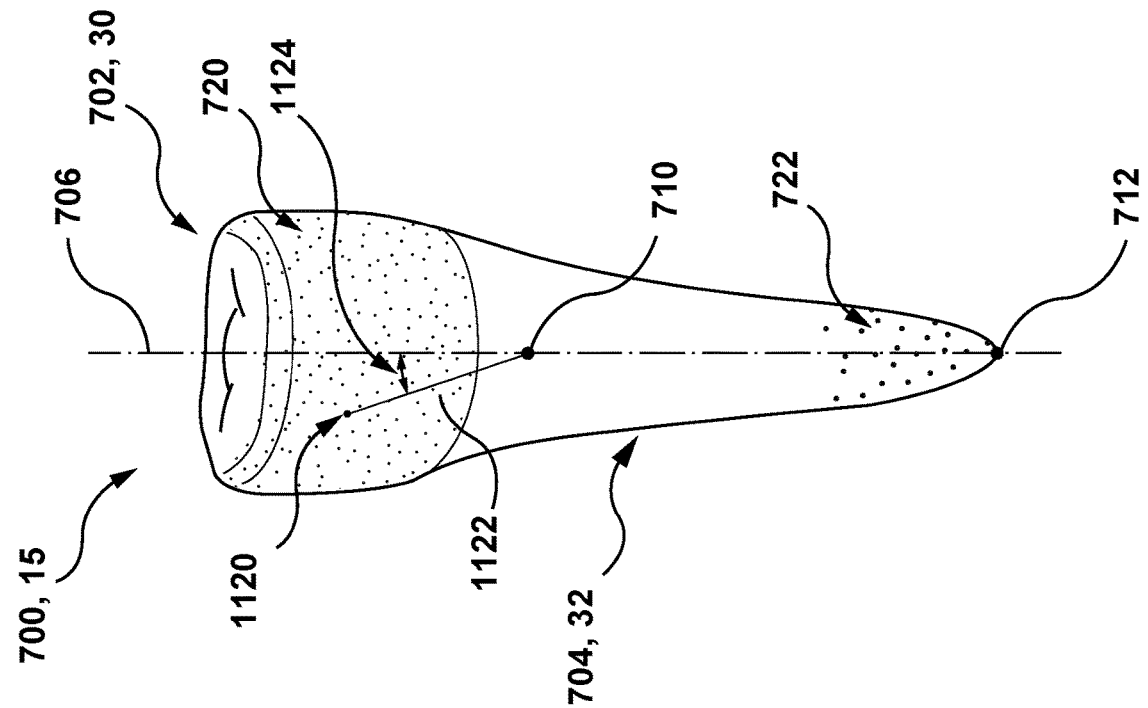
FIGS. 11A and 11B depict schematic diagrams for different approaches of determining, by the processor of FIG. 5, sets of additional crown reference points and additional root reference points for generating a plurality of crown reference points and a plurality of root reference points, respectively, according to certain non-limiting embodiments of the present technology.
Figure 11A:
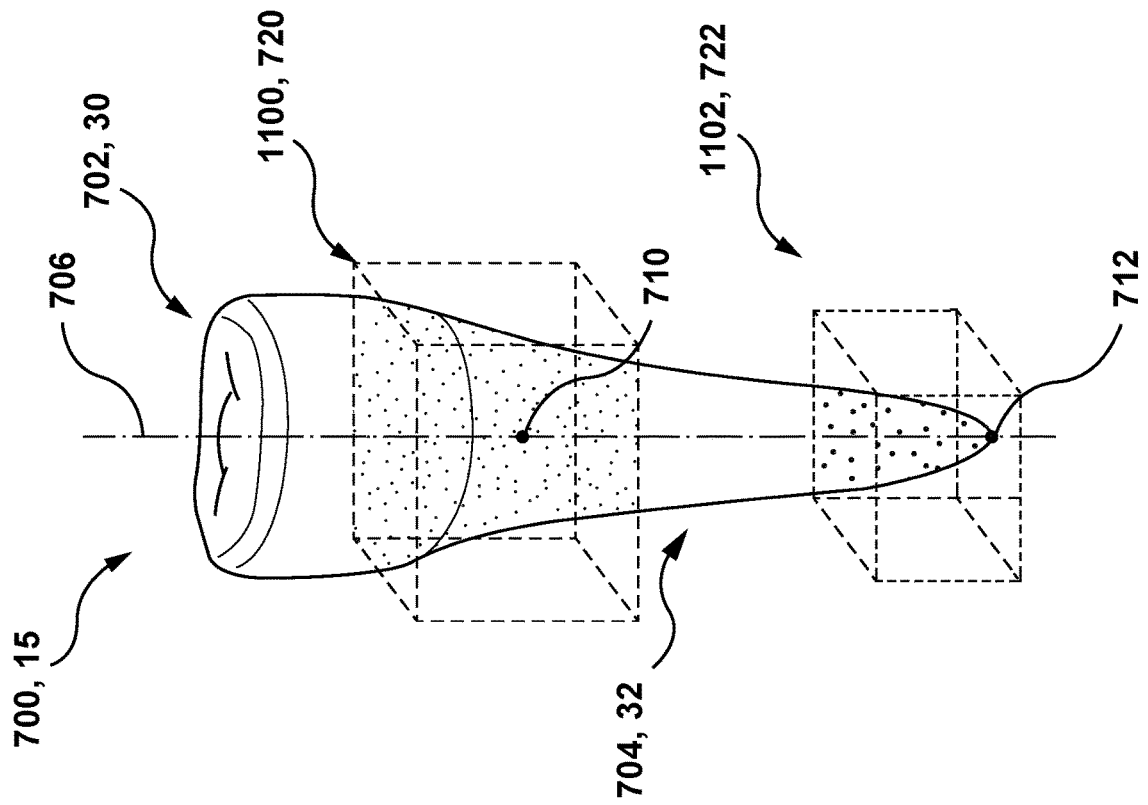

With reference to FIG. 11A, there is depicted a schematic diagram of a first approach for determining, by the processor 550, around the crown reference point 710, a set of additional crown reference points 720, in accordance with certain non-limiting embodiments of the present technology.

More specifically, in some non-limiting embodiments of the present technology, the processor 550 can be configured to (i) generate a crown bounding box 1100, originating in the crown reference point 710, around the tooth 3D digital model 700 of the given tooth 15; and (ii) determine the set of additional crown reference points 720 as being vertices of the tooth 3D digital model 700 encompassed by the crown bounding box 1100. However, in other non-limiting embodiments of the present technology, the processor 550 can be configured to determine the set of additional crown reference points 720 as being vertices only of the crown 3D digital model 702 of the crown portion 30 encompassed by the crown bounding box 1100.

Further, according to non-limiting embodiments of the present technology, the crown bounding box 1100 can have a predetermined height, such as 0.5 mm, 1 mm, 2 mm, or 5 mm, as example. However, in other non-limiting embodiments of the present technology, the height of the crown bounding box 1100 can be determined based on a trade-off between available computational resources of the processor 550 and a desired accuracy of determining the tooth trajectory of the given tooth 15.

Similarly, with continued reference to FIG. 11A, the processor 550 can be configured to determine the plurality of root reference points by determining a set of additional root reference points 722 around the root reference point 712. More specifically, the processor 550 can be configured to (i) generate a root bounding box 1102 originating in the root reference point 712, similarly to generating the crown bounding box 1100; and (ii) determine the set of additional root reference points 722 as being vertices of the root 3D digital model 704 of the root portion 32 of the given tooth 15 encompassed by the root bounding box 1102.

However, in other non-limiting embodiments of the present technology, the processor 550 can be configured to obtain the sets of additional reference points differently. With reference to FIG. 11B, there is depicted a schematic diagram of a second approach for determining, by the processor 550, the set of additional crown reference points 720, in accordance with certain non-limiting embodiments of the present technology.

More specifically, in these embodiments, the processor 550 can be configured to (i) for each one of the vertices of the crown 3D digital model 702, such as given crown vertex 1120, generate a respective line 1122; (ii) determine a respective angle 1124 between the respective line 1122 and the predetermined longitudinal axis 706; (iii) compare the respective angle 1124 to a predetermined angular threshold (such as 30 degrees, for example); and (iv) in response to the respective angle 1124 being equal to or greater than the predetermined angular threshold, determine the given crown vertex 1120 as one of the set of additional crown reference points 720. Similarly, the processor 550 can be configured to determine the set of additional root reference points 722.

Figure 12:
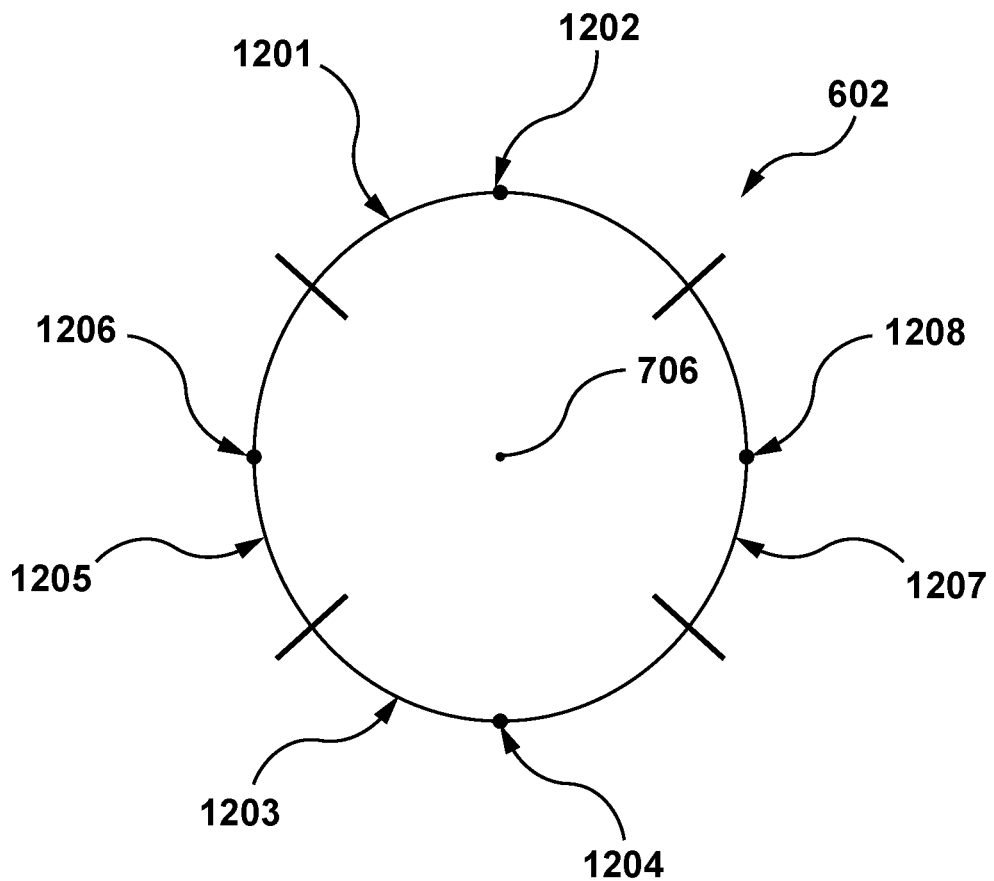
FIG. 12 depicts a top view of a tooth-gingiva segmentation loop associated with the given tooth for another approach to determining, by the processor of FIG. 5, the plurality of crown reference points.

In yet other non-limiting embodiments of the present technology, the processor 550 can be configured to determine the plurality of crown reference points as certain vertices defining the tooth-gingiva segmentation loop 602. With reference to FIG. 12, there is depicted a top view of the tooth-gingiva segmentation loop 602 for executing another approach for determining, by the processor 550, the plurality of crown reference points, in accordance with certain non-limiting embodiments of the present technology.

More specifically, in these embodiments, first, the processor 550 can be configured to identify, along a length of the tooth-gingiva segmentation loop 620, (1) a labial portion 1201; (2) a lingual portion 1203; (3) a mesial portion 1205; and (4) a distal portion 1207 of the tooth-gingiva segmentation loop 620. It is not limited how the processor 550 can be configured to identify these portions of the tooth-gingiva segmentation loop 620. For example, in some non-limiting embodiments of the present technology, the processor 550 can be configured to (i) identify respective portions of the surface of the crown portion 30 of the given tooth 15, and (ii) further identify the above portions of the tooth-gingiva segmentation loop 620 as those extending along a labial, lingual, mesial, and distal portions of the surface of the crown portion 30 of the given tooth 15. To that end, for example, the processor 550 can be configured to apply one or more approaches described in the U.S. patent application Ser. No. 17/720,409 filed on Apr. 14, 2022, entitled "SYSTEMS AND METHODS FOR DETERMINING A POSITION FOR AN ORTHODONTIC ATTACHMENT", the content of which is incorporated herein by reference in its entirety. More specifically, referring back to FIG. 7, for example, the processor 550 can be configured to (1) identify, within the tooth 3D digital model 700 of the given tooth 15, mesial and distal points (not depicted) on a surface of the crown portion 30; (2) generate a reference plane extending through the mesial and distal points and the predetermined longitudinal axis 706; (3) determine, at each one of the plurality of vertices representative of the crown portion 30, a respective normal vector (not depicted); (4) determine, a respective angle between a given normal vector and the reference plane; and (5) based on a value of the respective angle, determine the respective vertex of the plurality of vertices associated with the given normal vector as defining one of the labial, lingual, mesial, and distal portions of the surface of the crown portion 30.

Further, having identified the labial, lingual, mesial, and distal portions 1201, 1203, 1205, and 1207 along the length of the tooth-gingiva segmentation loop 620, the processor 550 can be configured to determine the plurality of crown reference points including at least one point within each one of the so identified portions of the tooth-gingiva segmentation loop 620, such as a first point 1202, a second point 1204, a third point 1206, and a fourth point 1208. In some non-limiting embodiments of the present technology, the processor 550 can be configured to determine a given point of the plurality of crown reference points, such as the first point 1202, as a vertex of the respective portion of the tooth-gingiva segmentation loop 620, that is, the labial portion 1201, representative of a maximum positive (convex) curvature of the labial portion 1201. However, in other non-limiting embodiments of the present technology, the processor 550 can be configured to determine the first point 1202 as a vertex of the labial portion 1201 representative of a maximum negative (concave) curvature thereof. In yet other non-limiting embodiments of the present technology, the processor 550 can be configured to identify both vertices as being ones of the plurality of crown reference points. In yet other example, the processor 550 can be configured to identify the first point 1202 as being a vertex of the labial portion 1201 positioned at a greatest distance form the predetermined longitudinal axis 706.

Further, as mentioned above, based on the so obtained plurality of crown reference points and plurality of root reference points, the processor 550 can be configured to generate the plurality of crown reference lines (not depicted) and the plurality of root reference points (not depicted) similarly to determining the crown reference line 1002 and the root reference line 1004 as described above with reference to FIG. 10. Further, the processor 550 can be configured to determine (1) the longest crown reference line from the plurality of crown reference lines as being representative of the crown trajectory of the crown portion 30 of the given tooth 15; and (2) the longest root reference line from the plurality of root reference lines as being representative of the root trajectory of the root portion 32 of the given tooth 15. Further, the processor 550 can be configured to determine the longer one of the longest crown reference line and the longest root reference line as being representative of the tooth trajectory of the given tooth 15. By so doing, as will become apparent from the description provided below, the risks of damaging the PDL 34 of the given tooth 15 can be even more mitigated.

Further, based on the so determine tooth trajectory, the processor 550 can be configured to determine steps of the orthodontic treatment to cause the given tooth 15 to move from the current position to the target position thereof. In some non-limiting embodiments of the present technology, the steps of the orthodontic treatment can be determined based on the predetermined safety distance threshold representative of a maximum possible displacement of the given tooth 15 along the tooth trajectory without causing damage to the PDL 34 thereof, as described above. To that end, the processor 550 can be configured to segment the crown reference line 1002 into a crown plurality of segments 1006 such that each one of the crown plurality of segments would not exceed the predetermined safety distance threshold.

In some non-limiting embodiments of the present technology, the processor 550 can be configured to optimize the orthodontic treatment by iteratively minimizing a number of segments in the crown plurality of segments 1006 such that a longest one thereof is no longer than the predetermined safety distance threshold. In other words, the processor 550 can be configured to maximize respective lengths of each one of the crown plurality of segments 1006, thereby reducing the number thereof. Also, in some non-limiting embodiments of the present technology, the processor 550 can be configured to determine the crown plurality of segments 1006 to be of an equal length.

Further, in some non-limiting embodiments of the present technology, the processor 550 can be configured to store data of crown plurality of steps in one of the solid-state drive 560 and the random-access memory 570 for further use in planning the orthodontic treatment.

For example, as noted hereinabove, using the data of the crown plurality of segments 1006, the processor 550 can be configured to determine respective forces to be exerted onto the given tooth 15 to cause the crown reference point 710 to move along each one of the crown plurality of segments 1006, thereby causing the given tooth 15 to move towards the target position thereof. Further, based on the so determined forces, the processor 550 can be configured to determine and further produce the respective configurations of orthodontic appliances, such as the aligner 20, configured to apply those forces onto the given tooth 15. For example, a given configuration of the aligner 20 can be applied to the lower teeth 11 to exert the respective force onto the given tooth 15 over a predetermined treatment period to cause the crown reference point 710 thereof to move along a respective one of the crown plurality of segments 1006. The predetermined treatment period may be determined based on time needed for the PDL 34 to recover after being stressed or strained by the tooth movement, along the respective one of the crown plurality of segments 1006, and securely fix the given tooth 15 to the alveolar bone 33 at the target position thereof, as described above. In some non-limiting embodiments of the present technology, the predetermined treatment period may comprise 14 days, as an example.

Thus, as it can further be appreciated from FIG. 10, while the crown reference point 710, under the force exerted on the given tooth 15 by the respective configuration of the aligner 20, would be caused to move along a given crown segment 1008 of the crown plurality of segments 1006, any point lying on the predetermined longitudinal axis 706 between the crown reference point 710 and the root reference point 712 would be caused to perform a shorter displacement along their respective trajectories.

Thus, by so doing, certain non-limiting embodiments of the present technology may allow preventing or minimizing damage of the PDL 34 of the given tooth 15 during the implementation of the orthodontic treatment.

Method

Figure 13:
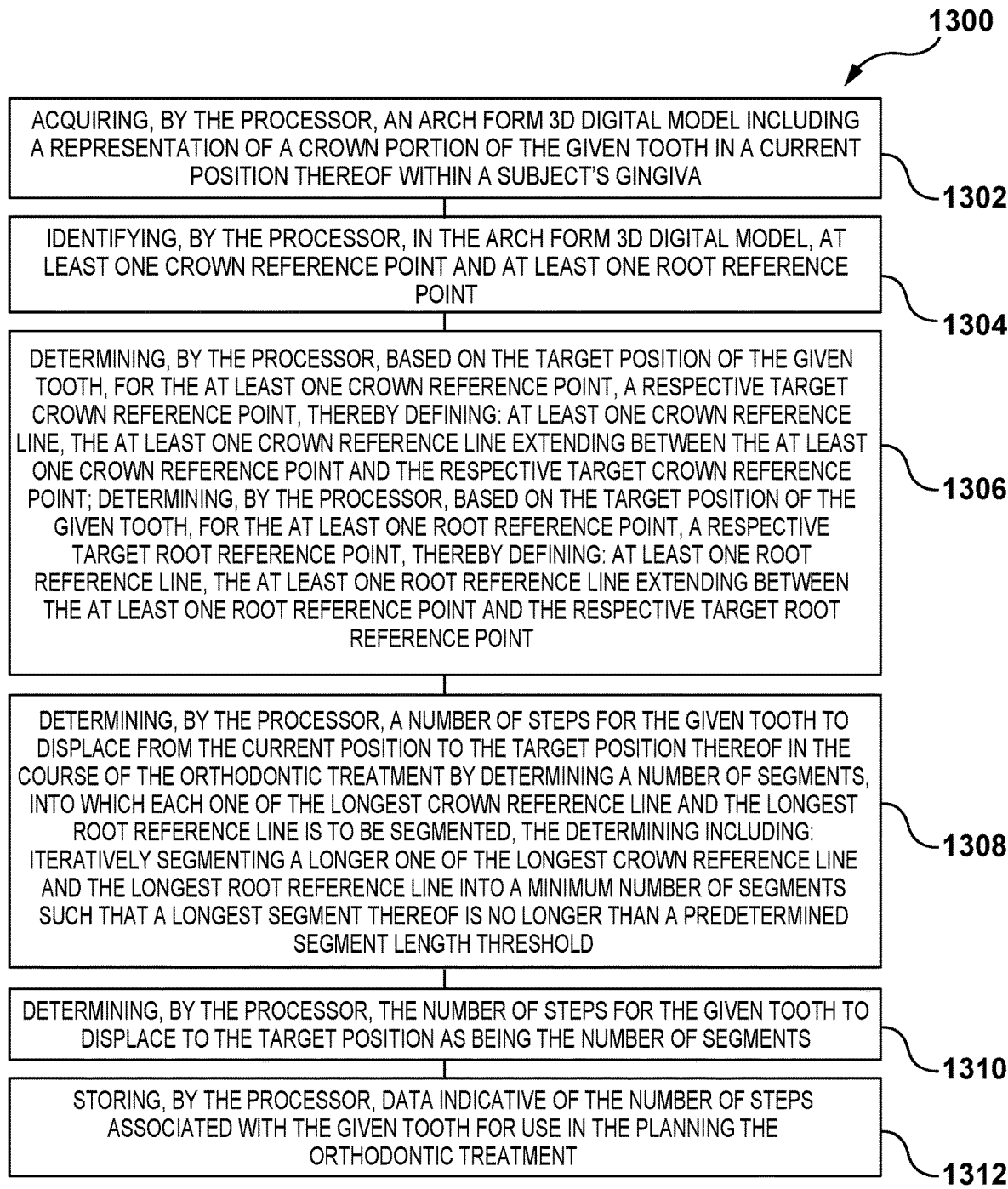
FIG. 13 depicts a flowchart of a method of determining the orthodontic treatment for the given tooth of the subject's teeth present in FIG. 1, according to certain embodiments of the present technology.

Given the architecture and the examples provided hereinabove, it is possible to execute a method for planning the orthodontic treatment subject's teeth, such as that for the given tooth 15. With reference now to FIG. 13, there is depicted a flowchart of a method 1300, according to certain non-limiting embodiments of the present technology. The method 1300 may be executed by the processor 550 of the system 400.

Step 1302: Acquiring, by the Processor, an Arch Form 3D Digital Model Including a Representation of a Crown Portion of the Given Tooth in a Current Position Thereof within a Subject's Gingiva According to certain non-limiting embodiments of the present technology, the method 1300 commences at step 1302 with the processor 500 being configured to acquire the arch form 3D digital model 600 of the lower arch form 10. Further, the processor 550 can be configured, based on the arch form 3D digital model 600, to generate tooth 3D digital model 700 of the given tooth 15 as described above with reference to FIGS. 6 and 7.

For example, in some non-limiting embodiments of the present technology, the processor 550 can be configured to (1) determine the tooth-gingiva segmentation loop 602 indicative of the intersection between the given tooth 15 and the lower gingiva 14, segment the crown 3D digital model 702 of the crown portion 30; (2) based on the crown 3D digital model 702, restore the root 3D digital model 704 of the root portion 32 of the given toot 15; and (3) merge the crown 3D digital model 702 and the root 3D digital model 704, thereby generating the tooth 3D digital model 700.

Further, in some non-limiting embodiments of the present technology, the processor 550 can be configured to obtain an indication of the predetermined longitudinal axis 706 associated with the given tooth 15. In some non-limiting embodiments of the present technology, as described above with reference to FIG. 7, the processor 550 can be configured to determine the predetermined longitudinal axis 706 as being indicative of the tooth axis 36 of the given tooth 15.

The method 1300 thus proceeds to step 1304.

Step 1304: Identifying, by the Processor, in the Arch Form 3D Digital Model, at Least One Crown Reference Point and at Least One Root Reference Point At step 1304, based on the data obtained at step 1102, the processor 550 can be configured to identify at least one crown reference point and at least one root reference points for tracking trajectories of the crown portion 30 and the root portion 32 of the given tooth 15, respectively. For example, the processor 550 con be configured to determine the crown reference point 710 and the root reference point 712 on the predetermined longitudinal axis 706 for determining the tooth trajectory of the given tooth 15, based on which the orthodontic treatment therefor can be planned.

According to certain non-limiting embodiments of the present technology, the processor 550 can be configured to determine the crown reference point 710 based on the tooth-gingiva segmentation loop 602. In some non-limiting embodiments of the present technology, the processor 550 can be configured to determine the crown reference point 710 as the center of the tooth-gingiva segmentation loop 602 using one the approaches described above with reference to FIGS. 8 and 9.

In additional non-limiting embodiments of the present technology, the processor 550 can further be configured to offset the crown reference point 710 along the predetermined longitudinal axis 706 towards the root portion 32 at the crown offset predetermined distance, which may be from around 0.2 mm to around 2 mm.

Figure 7:
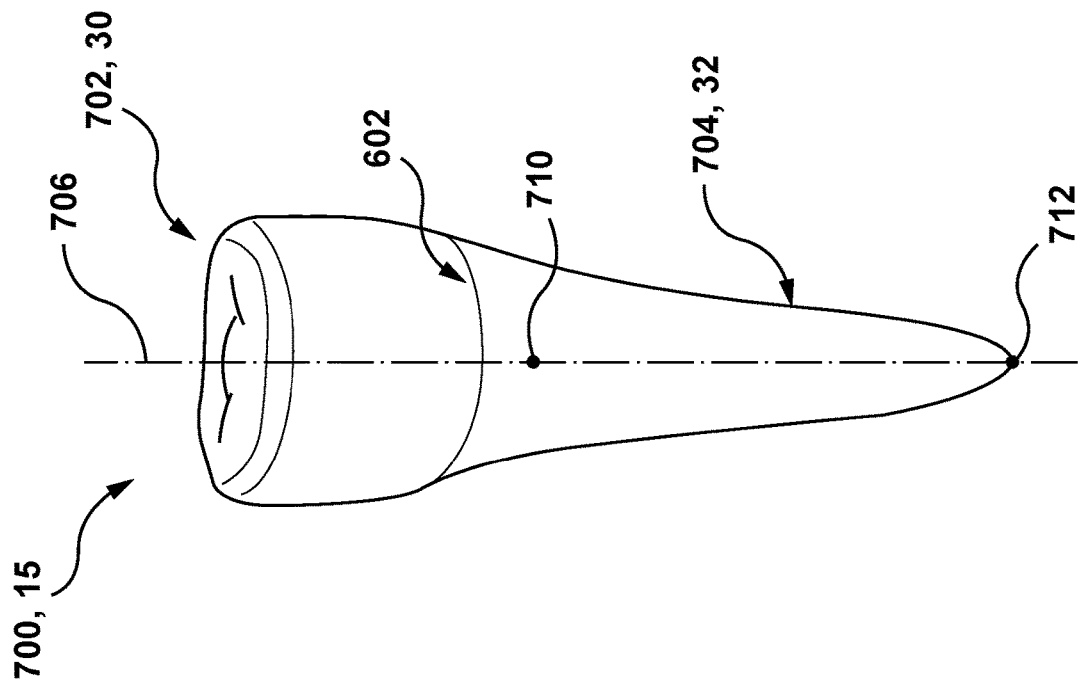
FIG. 7 depicts a 3D digital model of the given tooth of the subject isolated, by the processor of FIG. 5, from the 3D digital model of FIG. 6, in accordance with certain non-limiting embodiments of the present technology.

Further, in some non-limiting embodiments of the present technology, the processor 550 can be configured to determine the root reference point 712 on the predetermined longitudinal axis 706 as that corresponding to the apex 42 of the root portion 32 of the given tooth 15, as described further above with reference to FIG. 7. As noted above, in those non-limiting embodiments where the root portion 32 as more than one root, processor 550 can be configured to determine the root reference point 712 as that corresponding to an apex of a longest root of the root portion 32.

Further, in some non-limiting embodiments of the present technology, the processor 550 can further be configured to offset the root reference point 712 along the predetermined longitudinal axis 706 at the root offset predetermined distance towards the crown portion 30, as described above.

In some non-limiting embodiments of the present technology, the processor 550 can be configured to determine the root reference point 712 as being the CR point 38 as described above with reference to FIG. 3.

However, in other non-limiting embodiments of the present technology, the processor 550 can be configured to determine the plurality of crown reference points and the plurality of root reference points, as described above with reference to FIGS. 11A, 11B, and 12. More specifically, in some non-limiting embodiments of the present technology, the processor 550 can be configured to determine the plurality of crown reference points by obtaining the set of additional crown reference points 720 around the crown reference point 710 as described above with reference to FIGS. 11A and 11B. Similarly, the processor 550 can be configured to determine the plurality of root reference points. In alternative non-limiting embodiments of the present technology, the processor 550 can be configured to determine the plurality of crown reference points on the tooth-gingiva segmentation loop 620 as described above with reference to FIG. 12.

The method 1300 hence advances to step 1306.

Step 1306: Determining, by the Processor, Based on the Target Position of the Given Tooth, for the at Least One Crown Reference Point, a Respective Target Crown Reference Point, Thereby Defining: At Least One Crown Reference Line, the at Least One Crown Reference Line Extending Between the at Least One Crown Reference Point and the Respective Target Crown Reference Point; Determining, by the Processor, Based on the Target Position of the Given Tooth, for the at Least One Root Reference Point, a Respective Target Root Reference Point, Thereby Defining: At Least One Root Reference Line, the at Least One Root Reference Line Extending Between the at Least One Root Reference Point and the Respective Target Root Reference Point At step 1306, as described above with reference to FIG. 10, according to certain non-limiting embodiments of the present technology, the processor 550 can be configured to obtain the target position of the given tooth 15—such as that that would result from the given tooth 15 performing the given tooth movement 1010, as an example.

Further, based on the target position of the given tooth 15, the crown reference point 710 and the root reference point 712 determined at step 1104, the processor 550 can be configured to determine the crown trajectory and the root trajectory associated with the given tooth 15.

For example, by joining instances of the crown reference point 710 in the current position and in the target position of the given tooth 15, the processor 550 can be configured to define the crown reference line 1002 representative of the crown trajectory of the crown portion 30 of the given tooth 15. Similarly, by joining instances of the root reference point 712 in the current position and in the target position of the given tooth 15, the processor 550 can be configured to define the root reference line 1004 representative of the root trajectory of the root portion 32 of the given tooth 15.

Further, in those embodiments, where the processor 550 is configured to determine the plurality of crown reference points and the plurality of root reference points, at step 1306, similar to the crown reference line 1002 and the root reference line 1004, the processor 550 can be configured to determine the plurality of crown reference lines (not depicted) and the plurality of root reference points (not depicted). Further, the processor 550 can be configured to determine (1) the longest crown reference line from the plurality of crown reference lines as being representative of the crown trajectory of the crown portion 30 of the given tooth 15; and (2) the longest root reference line from the plurality of root reference lines as being representative of the root trajectory of the root portion 32 of the given tooth 15

The method 1300 thus proceeds to step 1308.

Step 1308: Determining, by the Processor, a Number of Steps for the Given Tooth to Displace from the Current Position to the Target Position Thereof in the Course of the Orthodontic Treatment by Determining a Number of Segments, into which Each One of the Longest Crown Reference Line and the Longest Root Reference Line is to be Segmented, the Determining Including: Iteratively Segmenting a Longer One of the Longest Crown Reference Line and the Longest Root Reference Line into a Minimum Number of Segments Such that a Longest Segment Thereof is No Longer than a Predetermined Segment Length Threshold Further, based on the so determined crown and root trajectories, at step 1108, the processor 550 can be configured to determine the tooth trajectory of the given tooth 15 for planning the orthodontic treatment. As mentioned above, in some non-limiting embodiments of the present technology, the processor 550 can be configured to determine the tooth trajectory as being the longer one out of the crown trajectory and the root trajectory associated with the given tooth 15.

Alternatively, as it can be appreciated, in those embodiments where the processor 550 is configured to determine the crown trajectory and the root trajectory as being represented by the longest crown reference line and the longest root reference line from the respective pluralities of reference lines, the processor 550 can be configured to determine the tooth trajectory for the given tooth 15 as being the linger one of the longest crown reference line and the longest root reference line.

Thus, according to the example depicted in FIG. 10, the processor 550 can be configured to determine the tooth trajectory as the crown trajectory thereof. Further, the processor 550 can be configured to segment the so determined tooth trajectory, thereby determining the number of steps of the orthodontic treatment to be applied to the given tooth 15. In some non-limiting embodiments of the present technology, the steps of the orthodontic treatment can be determined based on the predetermined safety distance threshold representative of a maximum possible displacement of the given tooth 15 along the tooth trajectory without causing damage to the PDL 34 thereof, as described above. To that end, the processor 550 can be configured to segment the crown reference line 1002 into the crown plurality of segments 1006 such that each one of the crown plurality of segments 1006 would not exceed the predetermined safety distance threshold.

In some non-limiting embodiments of the present technology, the processor 550 can be configured to optimize the orthodontic treatment by iteratively minimizing the number of segments in the crown plurality of segments 1006 such that the longest one thereof is no longer than the predetermined safety distance threshold. In other words, the processor 550 can be configured to maximize respective lengths of each one of the crown plurality of segments 1006, thereby reducing the number thereof. Also, in some non-limiting embodiments of the present technology, the processor 550 can be configured to determine the crown plurality of segments 1006 to be of an equal length.

The method 1300 hence advances to step 1310.

Step 1110: Determining, by the Processor, the Number of Steps for the Given Tooth to Displace to the Target Position as being the Number of Segments At step 1110, the processor 550 can be configured to determine the number of steps of the orthodontic treatment as the number of segments of the longer one out od the crown trajectory and the root trajectory, that is, in the example of FIG. 6, that of crown plurality of segments 1006.

The method 1300 thus proceeds to step 1312.

Step 1312: Storing, by the Processor, Data Indicative of the Number of Steps Associated with the Given Tooth for Use in the Planning the Orthodontic Treatment Finally, at step 1312, the processor can be configured to store data of the crown plurality of steps in one of the solid-state drive 560 and the random-access memory 570 for further use in planning the orthodontic treatment.

For example, as noted hereinabove, using the data of the crown plurality of segments 1006, the processor 550 can be configured to determine respective forces to be exerted onto the given tooth 15 to cause the crown reference point 710 to move along each one of the crown plurality of segments 1006, thereby causing the given tooth 15 to move towards the target position thereof. Further, based on the so determined forces, the processor 550 can be configured to determine and further produce the respective configurations of orthodontic appliances, such as the aligner 20, configured to apply those forces onto the given tooth 15, as described above.

Thus, certain non-limiting embodiments of the method 1300 may allow minimizing or preventing damage to the PDL 34 of the given tooth 15 during the orthodontic treatment increasing the safety thereof. Also, due to the optimization of the number of steps of the orthodontic treatment as described above, the method 1300 may allow reducing the overall time of implementation thereof without loss of safety.

The method 1300 thus terminates.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A computer-implemented method of planning an orthodontic treatment for a given tooth of a subject, the method being executable by a processor, the method comprising:
   acquiring, by the processor, an arch form 3D digital model including a representation of a crown portion of the given tooth in a current position thereof within a subject's gingiva;
   identifying, by the processor, in the arch form 3D digital model, at least one crown reference point and at least one root reference point,
   the at least one crown reference point being indicative of a first vertical boundary of a periodontal ligament around the given tooth at the crown portion thereof; and
   the at least one root reference point being indicative of a second vertical boundary of the periodontal ligament around the given tooth at a root portion thereof;

obtaining, by the processor, a target position of the given tooth within the arch form 3D digital model;

determining, by the processor, based on the target position of the given tooth, for the at least one crown reference point, a respective target crown reference point, thereby defining:

at least one crown reference line, the at least one crown reference line extending between the at least one crown reference point and the respective target crown reference point;

determining, by the processor, based on the target position of the given tooth, for the at least one root reference point, a respective target root reference point, thereby defining:

at least one root reference line, the at least one root reference line extending between the at least one root reference point and the respective target root reference point;

determining, from the at least one crown reference line, a longest crown reference line as being representative of a crown trajectory, along which the crown portion of the given tooth is to be moved while the given tooth is moving from the current position to the target position thereof;

determining, from the at least one root reference line, a longest root reference line as being representative of a root trajectory, along which the root portion of the given tooth is to be moved while the given tooth is moving from the current position to the target position thereof;

determining, by the processor, a number of steps for the given tooth to displace from the current position to the target position thereof in the course of the orthodontic treatment by determining a number of segments, into which each one of the longest crown reference line and the longest root reference line is to be segmented, the determining including:

iteratively segmenting a longer one of the longest crown reference line and the longest root reference line into a minimum number of segments such that a longest segment thereof is no longer than a predetermined segment length threshold;

determining, by the processor, the number of steps for the given tooth to displace to the target position as being the number of segments; and storing, by the processor, data indicative of the number of steps associated with the given tooth for use in the planning the orthodontic treatment.

2. The method of claim 1, wherein the identifying the at least one crown reference point comprises:

obtaining, by the processor, a segmentation loop, the segmentation loop segmenting, in the arch form 3D digital model, the crown portion of the given tooth from the subject's gingiva;

identifying, by the processor, along the segmentation loop, a mesial portion, a distal portion, a lingual portion, and a labial portion of the segmentation loop; and identifying the at least one crown reference point as being at least one of points representative of a respective maximum positive curvature value of a respective one of the mesial portion, the distal portion, the lingual portion, and the labial portion of the segmentation loop.

3. The method of claim 1, wherein the identifying the at least one crown reference point comprises:

obtaining, by the processor, data indicative of a predetermined longitudinal axis associated with the given tooth;

determining, by the processor, on the predetermined longitudinal axis, an initial crown reference point; and obtaining, by the processor, around the initial crown reference point, a set of crown reference points.

4. The method of claim 3, wherein the predetermined longitudinal reference axis is a central tooth axis of the given tooth having been predetermined based on the representation of the crown portion of the given tooth within the arch form 3D digital model.

5. The method of claim 3, wherein determining, on the predetermined longitudinal reference axis, the initial crown reference point comprises:

obtaining, by the processor, a segmentation loop, the segmentation loop segmenting, in the arch form 3D digital model, the crown portion of the given tooth from the subject's gingiva;

determining, by the processor, a center of the segmentation loop on the predetermined longitudinal reference axis of the given tooth; and offsetting the center of the segmentation loop along the predetermined longitudinal axis towards the root portion at a predetermined crown offset distance.

6. The method of claim 5, wherein the determining the center of the segmentation loop comprises:

projecting, over a respective normal vector, each vertex representative of the segmentation loop of the given tooth on the predetermined longitudinal reference axis; and determining the center of the segmentation loop as a midpoint amongst projected vertices on the predetermined longitudinal reference axis.

7. The method of claim 5, wherein the determining the center of the segmentation loop comprises:

generating, within the arch form 3D digital model, a bounding box around the segmentation loop; and determining the center of the segmentation loop as a center of a segment of the predetermined longitudinal reference axis formed by an intersection thereof with the bounding box.

8. The method of claim 3, wherein the arch form 3D digital model comprises a plurality of vertices representative of a surface of the crown portion of the given tooth, and wherein the obtaining, around the initial crown reference point, the set of crown reference points comprises:

generating, by the processor, around the crown portion of the given tooth a crown bounding box originating in the initial crown reference point, the crown bounding box being of a predetermined height; and determining, by the processor, the set of crown reference points as being vertices of the plurality of vertices encompassed by the crown bounding box.

9. The method of claim 3, wherein the arch form 3D digital model includes a plurality of vertices representative of a surface of the crown portion of the given tooth, and wherein the obtaining, around the initial crown reference point, the set of crown reference points comprises:

generating, by the processor, for each one the plurality of vertices representative of the crown portion, a respective line extending thereto from the initial crown reference point; and determining, by the processor, the set of crown reference points as being vertices of the plurality of vertices whose associated respective lines form respective angles with the predetermined longitudinal axis that are greater than a predetermined angular threshold.

10. The method of claim 1, wherein the identifying the at least one root reference point comprises:

obtaining, by the processor, data indicative of a predetermined longitudinal axis associated with the given tooth;

determining, by the processor, on the predetermined longitudinal axis, an initial root reference point; and obtaining, by the processor, around the initial root reference point, a set of root reference points.

11. The method of claim 10, wherein the determining, on the predetermined longitudinal reference axis, the initial root reference point includes determining, in the arch form 3D digital model, a point corresponding to a root apex of a longest root of the root portion of the given tooth.

12. The method of claim 11, wherein the determining the point corresponding to the root apex is based on reference data associated with the given tooth, the reference data comprising data of an approximate length associated with the root portion of the given tooth.

13. The method of claim 12, wherein the determining the initial root reference point further comprises offsetting the point corresponding to the root apex of the given tooth along the predetermined longitudinal reference axis towards the crown portion at a predetermined root offset distance.

14. The method of claim 10, wherein the initial root reference point is a center of resistance associated with the given tooth.

15. The method of claim 10, wherein the arch form 3D digital model further includes a plurality of vertices representative of a surface of the root portion of the given tooth, and wherein the obtaining, by the processor, around the initial root reference point, the set of root reference points comprises:

generating, by the processor, around the root portion of the given tooth a root bounding box originating in the initial root reference point, the root bounding box being of a predetermined height; and determining, by the processor, the set of root reference points as being vertices of the plurality of vertices encompassed by the root bounding box.

16. The method of claim 1, wherein the predetermined segment length threshold has been determined such that a movement of the given tooth along a given segment of any one of the longest crown reference line and the longest root reference line does not cause damage to the periodontal ligament of the given tooth.

17. The method of claim 1, wherein the orthodontic treatment includes applying a respective orthodontic appliance at each step of the number of steps.

18. The method of claim 11, wherein each one of the number of steps is of a same length.

19. The method of claim 11, wherein the applying the respective orthodontic appliance is for a predetermined treatment interval.

20. A system for planning an orthodontic treatment for a given tooth of a subject, the system including a processor and a non-transitory computer-readable medium storing instructions, the processor, upon executing the instructions, being configured to:

acquire an arch form 3D digital model including a representation of a crown portion of the given tooth in a current position thereof within a subject's gingiva;

identifying, by the processor, in the arch form 3D digital model, at least one crown reference point and at least one root reference point, the at least one crown reference point being indicative of a first vertical boundary of a periodontal ligament around the given tooth at the crown portion thereof; and the at least one root reference point being indicative of a second vertical boundary of the periodontal ligament around the given tooth at a root portion thereof;

obtain a target position of the given tooth within the arch form 3D digital model;

determine, based on the target position of the given tooth, for the at least one crown reference point, a respective target crown reference point, thereby defining:

at least one crown reference line, the at least one crown reference line extending between the at least one crown reference point and the respective target crown reference point;

determine, based on the target position of the given tooth, for the at least one root reference point, a respective target root reference point, thereby defining:

at least one root reference line, the at least one root reference line extending between the at least one root reference point and the respective target root reference point;

determine, from the at least one crown reference line, a longest crown reference line as being representative of a crown trajectory, along which the crown portion of the given tooth is to be moved while the given tooth is moving from the current position to the target position thereof;

determine, from the at least one root reference line, a longest root reference line as being representative of a root trajectory, along which the root portion of the given tooth is to be moved while the given tooth is moving from the current position to the target position thereof;

determine a number of steps for the given tooth to displace from the current position to the target position thereof in the course of the orthodontic treatment by determining a number of segments, into which each one of the longest crown reference line and the longest root reference line is to be segmented, the determining including:

iteratively segmenting a longer one of the longest crown reference line and the longest root reference line into a minimum number of segments such that a longest segment thereof is no longer than a predetermined segment length threshold;

determine the number of steps for the given tooth to displace to the target position as being the number of segments; and store data indicative of the number of steps associated with the given tooth for use in the planning the orthodontic treatment.

* * * * *